US012799163B2

(12) United States Patent
Zhang et al.

(10) Patent No.: US 12,799,163 B2
(45) Date of Patent: Nov. 17, 2026

(54) COMBINATION OF PEPTIDE LINKERS FOR PROTEIN COVALENT SELF-ASSEMBLY USING SPONTANEOUS ISOPEPTIDE BOND

(71) Applicant: SUN YAT-SEN UNIVERSITY, Guangdong (CN)

(72) Inventors: Hui Zhang, Guangdong (CN); Xiantao Zhang, Guangdong (CN)

(73) Assignee: SUN YAT-SEN UNIVERSITY, Guangdong (CN)

( * ) Notice: Subject to any disclaimer, the term of this patent is extended or adjusted under 35 U.S.C. 154(b) by 532 days.

(21) Appl. No.: 18/556,677

(22) PCT Filed: Mar. 28, 2022

(86) PCT No.: PCT/CN2022/083430
§ 371 (c)(1),
(2) Date: Oct. 23, 2023

(87) PCT Pub. No.: WO2022/222700
PCT Pub. Date: Oct. 27, 2022

(65) Prior Publication Data

US 2024/0132545 A1 Apr. 25, 2024
US 2024/0228541 A9 Jul. 11, 2024

(30) Foreign Application Priority Data

Apr. 23, 2021 (CN) ......................... 202110444350.7
Jul. 31, 2021 (CN) ......................... 202110876301.0

(51) Int. Cl.
*C07K 7/00* (2006.01)
*C07K 7/08* (2006.01)
*C12N 15/63* (2006.01)

(52) U.S. Cl.
CPC ................ *C07K 7/08* (2013.01); *C12N 15/63* (2013.01)

(58) Field of Classification Search
CPC .... C07K 7/08; C07K 2319/70; C07K 14/315; C07K 2319/00; C07K 14/00; C07K 1/00; C12N 15/63; C12N 15/635
See application file for complete search history.

(56) References Cited

FOREIGN PATENT DOCUMENTS

| | | |
|---|---|---|
| CN | 113621031 | 11/2021 |
| WO | 2011098772 | 8/2011 |
| WO | 2016193746 | 12/2016 |
| WO | 2018197854 | 11/2018 |

OTHER PUBLICATIONS

Oppegaard et al. (Clinical and molecular characteristics of infective β-hemolytic streptococcal endocarditis, Diagnostic Microbiology and Infectious Disease 89 (2017) 135-142).*
S. Lee et al., "*Streptococcus dysgalactiae* strain GCH3 10, whole genome shotgun sequence", GenBank: WHSD01000010, Oct. 28, 2019, pp. 1-60.
R.P Novick, "Lpxtg cell wall anchor domain-containing protein [Gardnerella vaginalis]", GenBank: WP_165847589, Mar. 20, 2020, pp. 1-1.
N. Varghese et al., "Cna protein B-type domain-containing protein, partial [*Peptostreptococcus* sp. D1]", GenBank: SFE28504, Oct. 31, 2016, pp. 1-1.
*Streptococcus Anginosus*, "hypothetical protein [*Streptococcus anginosus*]", GenBank: WP_020999873, Sep. 4, 2013, pp. 1-2.
"International Search Report (Form PCT/ISA/210) of PCT/CN2022/083430," mailed on Jun. 24, 2022, with English translation thereof, pp. 1-8.

* cited by examiner

*Primary Examiner* — Jeanette M Lieb
(74) *Attorney, Agent, or Firm* — JCIPRNET

(57) ABSTRACT

Disclosed is a combination of peptide linkers for protein covalent self-assembly using a spontaneous isopeptide bond, including a peptide linker 1 and a peptide linker 2. The peptide linker 1 contains a peptide chain having an amino acid sequence as shown in SEQ ID NO: 5, and the peptide linker 2 contains any one or more of peptide chains having amino acid sequences as shown in SEQ ID NOs: 11, 13, 14, and 46. The present disclosure constructs a novel protein self-assembly system based on an isopeptide bond, which effectively solves the problem of low binding efficiency of an existing SpyTag/SpyCatcher system, can significantly improve the reaction efficiency of molecules or components fused to a peptide tag and polypeptide thereof, and has a binding efficiency stronger than that of a SpyTag003/SpyCatcher003 system.

14 Claims, 12 Drawing Sheets

Specification includes a Sequence Listing.

SEQUENCE LISTING

```
<160> NUMBER OF SEQ ID NOS: 49

<210> SEQ ID NO 1
<211> LENGTH: 101
<212> TYPE: PRT
<213> ORGANISM: Artificial Sequence
<220> FEATURE:
<223> OTHER INFORMATION: amino acid sequence of GvCatcher
```

<400> SEQUENCE: 1

Met Val Asp Lys Leu Lys Glu Val Pro Thr Ser Thr Lys Val Lys Phe
1 5 10 15

Ser Lys Lys Ala Leu Thr Glu Asn Gly Glu Asp Leu Lys Gly Ala Thr
20 25 30

Ile Gln Leu Thr Lys Ala Asp Gly Ser Leu Val Lys Lys Trp Val Thr
35 40 45

Asp Gly Thr Val Thr Glu Phe Glu Leu Lys Asp Gly Lys Tyr Thr Phe
50 55 60

Thr Glu Thr Ser Ala Pro Ala Lys Tyr Gln Val Ala Thr Ala Ile Thr
65 70 75 80

Phe Glu Val Lys Asn Gly Lys Ala Ile Val Lys Gly Ile Ala Val Thr
85 90 95

Gly Asn Thr Ile Val
100

<210> SEQ ID NO 2
<211> LENGTH: 99
<212> TYPE: PRT
<213> ORGANISM: Artificial Sequence
<220> FEATURE:
<223> OTHER INFORMATION: amino acid sequence of GbCatcher

<400> SEQUENCE: 2

Val Val Thr Asp Gly Tyr Ser Ser His Asp Ile Asn Ile Ser Lys Ala
1 5 10 15

Asp Ile Asp Gly Asn Glu Ile Ala Gly Ala Lys Ile Val Leu Thr Asp
20 25 30

Lys Ala Gly Lys Gln Ile Asp Ser Trp Thr Ser Thr Lys Glu Leu His
35 40 45

Lys Val Ser Leu Lys Pro Gly Thr Tyr Ile Phe Lys Glu Thr Leu Ala
50 55 60

Pro Glu Gly Phe Glu Val Val Thr Asp Ile Thr Phe Thr Val Asn Val
65 70 75 80

Asp Gly Thr Ile Thr Val Asn Asp Lys Gln Ala Lys Val Asn Asn Asp
85 90 95

Gly Val Leu

<210> SEQ ID NO 3
<211> LENGTH: 92
<212> TYPE: PRT
<213> ORGANISM: Artificial Sequence
<220> FEATURE:
<223> OTHER INFORMATION: amino acid sequence of PsCatcher

<400> SEQUENCE: 3

Glu Lys Thr Lys Val Lys Phe Ser Lys Lys Ala Leu Thr Ala Asn Gly
1 5 10 15

Glu Glu Leu Lys Gly Ala Thr Ile Lys Leu Thr Lys Glu Asn Gly Thr
20 25 30

Val Ile Lys Glu Trp Val Thr Asp Gly Lys Leu Thr Glu Phe Glu Leu
35 40 45

Glu Asp Gly Ser Tyr Thr Phe Thr Glu Ile Ser Ala Pro Asp Lys Tyr
50 55 60

Gln Val Ala Thr Ala Ile Thr Phe Glu Val Lys Ala Gly Lys Val Leu
65 70 75 80

Val Thr Gly Thr Glu Val Lys Gly Asn Thr Ile Val 85 90

<210> SEQ ID NO 4
<211> LENGTH: 94
<212> TYPE: PRT
<213> ORGANISM: Artificial Sequence
<220> FEATURE:
<223> OTHER INFORMATION: amino acid sequence of SaCatcher

<400> SEQUENCE: 4

Ser Thr Pro Ser Thr Lys Val Lys Phe Ser Lys Lys Ala Leu Thr Glu
1 5 10 15

Asn Gly Glu Glu Leu Lys Gly Ala Thr Ile Arg Leu Thr Lys Glu Asp
20 25 30

Gly Ser Leu Val Lys Glu Trp Val Thr Asp Gly Thr Val Lys Glu Phe
35 40 45

Glu Leu Lys Asp Gly Lys Tyr Thr Phe Thr Glu Ile Ser Ala Pro Asp
50 55 60

Lys Tyr Gln Val Ala Thr Ala Ile Thr Phe Glu Val Lys Asn Gly Lys
65 70 75 80

Val Ile Val Lys Gly Ile Glu Val Thr Gly Asn Thr Ile Val
85 90

<210> SEQ ID NO 5
<211> LENGTH: 106
<212> TYPE: PRT
<213> ORGANISM: Artificial Sequence
<220> FEATURE:
<223> OTHER INFORMATION: amino acid sequence of SdCatcher

<400> SEQUENCE: 5

Ser Gly Glu Thr Gly Gln Ser Gly Asn Thr Thr Ile Glu Glu Asp Ser
1 5 10 15

Thr Thr His Val Lys Phe Ser Lys Arg Asp Ile Asn Gly Lys Glu Leu
20 25 30

Ala Gly Ala Met Ile Glu Leu Arg Asn Leu Ser Gly Gln Thr Ile Gln
35 40 45

Ser Trp Val Ser Asp Gly Thr Val Lys Asp Phe Tyr Leu Met Pro Gly
50 55 60

Thr Tyr Gln Phe Val Glu Thr Ala Ala Pro Glu Gly Tyr Glu Leu Ala
65 70 75 80

Ala Pro Ile Thr Phe Thr Ile Asp Glu Lys Gly Gln Ile Trp Val Asp
85 90 95

Ser Thr Leu Ile Val Gly Asp Asp Pro Ile
100 105

<210> SEQ ID NO 6
<211> LENGTH: 105
<212> TYPE: PRT
<213> ORGANISM: Artificial Sequence
<220> FEATURE:
<223> OTHER INFORMATION: amino acid sequence of AhCatcher

<400> SEQUENCE: 6

Ile Thr Asp Lys Glu Thr Gly Glu Asp Ile Tyr Leu Val Lys Asp Asp
1 5 10 15

Val Thr Arg Val Ser Val Lys Lys Met Asp Ile Thr Gly Gln Lys Glu
20 25 30

Val Ala Gly Ala Arg Leu Leu Leu Lys Asp Lys Glu Gly Asn Val Ile
35 40 45

Glu Ser Trp Met Ser Thr Thr Glu Ala Arg Val Phe Glu Gln Lys Leu
50 55 60

Ile Ala Gly Glu Thr Tyr Thr Leu Thr Glu Val Thr Ala Pro Ser Gly
65 70 75 80

Tyr Glu Val Ala Ala Asp Ile Thr Phe Thr Val Asn Lys Asp Gly Thr
85 90 95

Val Ser Val Asp Gly Lys Ala Val Asp
100 105

<210> SEQ ID NO 7
<211> LENGTH: 100
<212> TYPE: PRT
<213> ORGANISM: Artificial Sequence
<220> FEATURE:
<223> OTHER INFORMATION: amino acid sequence of CpCatcher

<400> SEQUENCE: 7

Asn Asn Gln Lys Ser Glu Val Leu Lys Leu Asn Ile Ile Asp Asp Leu
1 5 10 15

Pro Lys Glu Val Leu Phe Ser Lys His Asp Ile Ala Gly Asn Glu Leu
20 25 30

Ala Gly Ala Thr Ile Glu Leu Ser Asn Lys Ala Asp Gly Lys Val Ile
35 40 45

Asp Thr Trp Val Ser Asp Gly Gln Gly Ala His Thr Phe Asn Leu Lys
50 55 60

Pro Gly Asn Tyr Val Phe Thr Glu Lys Ala Ala Pro Glu Gly Tyr Glu
65 70 75 80

Val Ala Thr Ala Ile Asn Phe Thr Val Asn Pro Asp Gly Thr Val Thr
85 90 95

Ser Asp Asp Val
100

<210> SEQ ID NO 8
<211> LENGTH: 103
<212> TYPE: PRT
<213> ORGANISM: Artificial Sequence
<220> FEATURE:
<223> OTHER INFORMATION: amino acid sequence of RSCatcher

<400> SEQUENCE: 8

Thr Phe Thr Ile Asp Lys Thr Gly Lys Val Leu Val Asn Gly Glu Asp
1 5 10 15

Val Asn Gly Gln Val Thr Met Tyr Asp Ala Ala Leu Gly Asp Val Val
20 25 30

Ile Ser Lys Arg Ala Val Asn Gly Thr Glu Glu Leu Glu Gly Ala Ser
35 40 45

Leu Lys Ile Thr Asp Ala Asp Gly Lys Thr Val Ala Glu Trp Val Ser
50 55 60

Asp Ser Thr Pro Lys Thr Ile Gln Leu Asp Ala Gly Thr Tyr Thr Leu
65 70 75 80

Thr Glu Glu Thr Ala Pro Asp Gly Tyr Thr Val Ala Glu Ser Ile Glu
85 90 95

Phe Val Val Asp Ala Ala Gly
100

<210> SEQ ID NO 9
<211> LENGTH: 110
<212> TYPE: PRT

<213> ORGANISM: Artificial Sequence
<220> FEATURE:
<223> OTHER INFORMATION: amino acid sequence of ScoCatcher

<400> SEQUENCE: 9

```
Thr Val Glu Asp Thr Ser Glu Val Gln Lys Val Glu Met Lys Asp Asp
1               5                   10                  15

Val Thr Lys Val Gln Ile Ser Lys Thr Asp Ile Ser Gly Lys Glu Leu
            20                  25                  30

Pro Gly Ala Lys Leu Thr Ile Leu Asp Lys Asp Gly Lys Thr Val Glu
        35                  40                  45

Ser Trp Thr Ser Glu Glu Lys Pro His Tyr Ile Glu Met Leu Pro Ile
    50                  55                  60

Gly Glu Tyr Thr Leu Arg Glu Glu Thr Ala Pro Asp Gly Tyr Leu Val
65                  70                  75                  80

Ala Glu Asp Val Lys Phe Thr Val Lys Asp Thr Gly Glu Ile Gln Lys
                85                  90                  95

Val Val Met Lys Asp Glu Val Lys Pro Thr Ala Thr Pro Thr
            100                 105                 110
```

<210> SEQ ID NO 10
<211> LENGTH: 105
<212> TYPE: PRT
<213> ORGANISM: Artificial Sequence
<220> FEATURE:
<223> OTHER INFORMATION: amino acid sequence of SpnCatcher

<400> SEQUENCE: 10

```
Gly Asn Thr Ile Val Met Val Asp Lys Leu Lys Glu Leu Pro Pro Pro
1               5                   10                  15

Pro Ser Thr Pro Pro Thr Lys Val Lys Phe Ser Lys Lys Ala Leu Thr
            20                  25                  30

Glu Asn Gly Glu Glu Leu Lys Gly Ala Thr Ile Arg Leu Thr Lys Glu
        35                  40                  45

Asp Gly Ser Leu Val Glu Glu Trp Val Thr Asp Gly Thr Val Lys Glu
    50                  55                  60

Phe Glu Leu Lys Asp Gly Lys Tyr Thr Phe Thr Glu Ile Ser Ala Pro
65                  70                  75                  80

Ala Lys Tyr Gln Val Ala Thr Ala Ile Thr Phe Glu Val Lys Asn Gly
                85                  90                  95

Lys Ala Ile Val Lys Gly Ile Glu Val
            100                 105
```

<210> SEQ ID NO 11
<211> LENGTH: 15
<212> TYPE: PRT
<213> ORGANISM: Artificial Sequence
<220> FEATURE:
<223> OTHER INFORMATION: amino acid sequence of GvTag

<400> SEQUENCE: 11

```
Asn Thr Ile Val Met Val Asp Lys Leu Lys Glu Val Pro Thr Pro
1               5                   10                  15
```

<210> SEQ ID NO 12
<211> LENGTH: 13
<212> TYPE: PRT
<213> ORGANISM: Artificial Sequence
<220> FEATURE:
<223> OTHER INFORMATION: amino acid sequence of GbTag

<400> SEQUENCE: 12

Thr Asn Ile Glu Phe Val Asp Gly Asn Lys Pro His Lys
1 5 10

<210> SEQ ID NO 13
<211> LENGTH: 13
<212> TYPE: PRT
<213> ORGANISM: Artificial Sequence
<220> FEATURE:
<223> OTHER INFORMATION: amino acid sequence of PsTag

<400> SEQUENCE: 13

Asn Thr Ile Val Met Val Asp Lys Leu Lys Lys Thr Pro
1 5 10

<210> SEQ ID NO 14
<211> LENGTH: 15
<212> TYPE: PRT
<213> ORGANISM: Artificial Sequence
<220> FEATURE:
<223> OTHER INFORMATION: amino acid sequence of SaTag

<400> SEQUENCE: 14

Asn Thr Ile Val Met Val Asp Lys Leu Lys Glu Leu Pro Pro Pro
1 5 10 15

<210> SEQ ID NO 15
<211> LENGTH: 13
<212> TYPE: PRT
<213> ORGANISM: Artificial Sequence
<220> FEATURE:
<223> OTHER INFORMATION: amino acid sequence of SdTag

<400> SEQUENCE: 15

Asp Pro Ile Val Met Ile Asp Asn Asp Lys Pro Ile Thr
1 5 10

<210> SEQ ID NO 16
<211> LENGTH: 13
<212> TYPE: PRT
<213> ORGANISM: Artificial Sequence
<220> FEATURE:
<223> OTHER INFORMATION: amino acid sequence of AhTag

<400> SEQUENCE: 16

Asn Glu Ile Val Met Lys Asp Glu Thr Thr Pro Val Gly
1 5 10

<210> SEQ ID NO 17
<211> LENGTH: 13
<212> TYPE: PRT
<213> ORGANISM: Artificial Sequence
<220> FEATURE:
<223> OTHER INFORMATION: amino acid sequence of CpTag

<400> SEQUENCE: 17

Asn His Val Val Met Val Asp Gly Tyr Ala Pro Lys Glu
1 5 10

<210> SEQ ID NO 18
<211> LENGTH: 13
<212> TYPE: PRT
<213> ORGANISM: Artificial Sequence
<220> FEATURE:
<223> OTHER INFORMATION: amino acid sequence of RSTag

<400> SEQUENCE: 18

```
Asp Gln Ile Val Met Val Asp Val Ala Lys Thr Thr Thr
1               5                   10


<210> SEQ ID NO 19
<211> LENGTH: 13
<212> TYPE: PRT
<213> ORGANISM: Artificial Sequence
<220> FEATURE:
<223> OTHER INFORMATION: amino acid sequence of ScoTag

<400> SEQUENCE: 19

Gln Lys Val Val Met Lys Asp Glu Val Lys Pro Thr Ala
1               5                   10


<210> SEQ ID NO 20
<211> LENGTH: 13
<212> TYPE: PRT
<213> ORGANISM: Artificial Sequence
<220> FEATURE:
<223> OTHER INFORMATION: amino acid sequence of SpnTag

<400> SEQUENCE: 20

Asn Thr Ile Val Met Val Asp Lys Leu Lys Glu Leu Pro
1               5                   10


<210> SEQ ID NO 21
<211> LENGTH: 267
<212> TYPE: PRT
<213> ORGANISM: Artificial Sequence
<220> FEATURE:
<223> OTHER INFORMATION: amino acid sequence of the fusion protein
      GvCatcher-HPF

<400> SEQUENCE: 21

Met Val Asp Lys Leu Lys Glu Val Pro Thr Ser Thr Lys Val Lys Phe
1               5                   10                  15

Ser Lys Lys Ala Leu Thr Glu Asn Gly Glu Asp Leu Lys Gly Ala Thr
            20                  25                  30

Ile Gln Leu Thr Lys Ala Asp Gly Ser Leu Val Lys Lys Trp Val Thr
        35                  40                  45

Asp Gly Thr Val Thr Glu Phe Glu Leu Lys Asp Gly Lys Tyr Thr Phe
    50                  55                  60

Thr Glu Thr Ser Ala Pro Ala Lys Tyr Gln Val Ala Thr Ala Ile Thr
65                  70                  75                  80

Phe Glu Val Lys Asn Gly Lys Ala Ile Val Lys Gly Ile Ala Val Thr
                85                  90                  95

Gly Asn Thr Ile Val Gly Ser Gly Asp Ile Ile Lys Leu Leu Asn Glu
            100                 105                 110

Gln Val Asn Lys Glu Met Gln Ser Ser Asn Leu Tyr Met Ser Met Ser
        115                 120                 125

Ser Trp Cys Tyr Thr His Ser Leu Asp Gly Ala Gly Leu Phe Leu Phe
    130                 135                 140

Asp His Ala Ala Glu Glu Tyr Glu His Ala Lys Lys Leu Ile Ile Phe
145                 150                 155                 160

Leu Asn Glu Asn Asn Val Pro Val Gln Leu Thr Ser Ile Ser Ala Pro
                165                 170                 175

Glu His Lys Phe Glu Gly Leu Thr Gln Ile Phe Gln Lys Ala Tyr Glu
            180                 185                 190

His Glu Gln His Ile Ser Glu Ser Ile Asn Asn Ile Val Asp His Ala
        195                 200                 205
```

```
Ile Lys Ser Lys Asp His Ala Thr Phe Asn Phe Leu Gln Trp Tyr Val
    210                 215                 220

Ala Glu Gln His Glu Glu Glu Val Leu Phe Lys Asp Ile Leu Asp Lys
225                 230                 235                 240

Ile Glu Leu Ile Gly Asn Glu Asn His Gly Leu Tyr Leu Ala Asp Gln
                245                 250                 255

Tyr Val Lys Gly Ile Ala Lys Ser Arg Lys Ser
            260                 265


<210> SEQ ID NO 22
<211> LENGTH: 265
<212> TYPE: PRT
<213> ORGANISM: Artificial Sequence
<220> FEATURE:
<223> OTHER INFORMATION: amino acid sequence of the fusion protein
      GbCatcher-HPF

<400> SEQUENCE: 22

Val Val Thr Asp Gly Tyr Ser Ser His Asp Ile Asn Ile Ser Lys Ala
1               5                   10                  15

Asp Ile Asp Gly Asn Glu Ile Ala Gly Ala Lys Ile Val Leu Thr Asp
            20                  25                  30

Lys Ala Gly Lys Gln Ile Asp Ser Trp Thr Ser Thr Lys Glu Leu His
        35                  40                  45

Lys Val Ser Leu Lys Pro Gly Thr Tyr Ile Phe Lys Glu Thr Leu Ala
    50                  55                  60

Pro Glu Gly Phe Glu Val Val Thr Asp Ile Thr Phe Thr Val Asn Val
65                  70                  75                  80

Asp Gly Thr Ile Thr Val Asn Asp Lys Gln Ala Lys Val Asn Asn Asp
                85                  90                  95

Gly Val Leu Gly Ser Gly Asp Ile Ile Lys Leu Leu Asn Glu Gln Val
            100                 105                 110

Asn Lys Glu Met Gln Ser Ser Asn Leu Tyr Met Ser Met Ser Ser Trp
        115                 120                 125

Cys Tyr Thr His Ser Leu Asp Gly Ala Gly Leu Phe Leu Phe Asp His
    130                 135                 140

Ala Ala Glu Glu Tyr Glu His Ala Lys Lys Leu Ile Ile Phe Leu Asn
145                 150                 155                 160

Glu Asn Asn Val Pro Val Gln Leu Thr Ser Ile Ser Ala Pro Glu His
                165                 170                 175

Lys Phe Glu Gly Leu Thr Gln Ile Phe Gln Lys Ala Tyr Glu His Glu
            180                 185                 190

Gln His Ile Ser Glu Ser Ile Asn Asn Ile Val Asp His Ala Ile Lys
        195                 200                 205

Ser Lys Asp His Ala Thr Phe Asn Phe Leu Gln Trp Tyr Val Ala Glu
    210                 215                 220

Gln His Glu Glu Glu Val Leu Phe Lys Asp Ile Leu Asp Lys Ile Glu
225                 230                 235                 240

Leu Ile Gly Asn Glu Asn His Gly Leu Tyr Leu Ala Asp Gln Tyr Val
                245                 250                 255

Lys Gly Ile Ala Lys Ser Arg Lys Ser
            260                 265


<210> SEQ ID NO 23
<211> LENGTH: 258
<212> TYPE: PRT
```

<213> ORGANISM: Artificial Sequence
<220> FEATURE:
<223> OTHER INFORMATION: amino acid sequence of the fusion protein PsCatcher-HPF

<400> SEQUENCE: 23

Glu Lys Thr Lys Val Lys Phe Ser Lys Lys Ala Leu Thr Ala Asn Gly
1 5 10 15

Glu Glu Leu Lys Gly Ala Thr Ile Lys Leu Thr Lys Glu Asn Gly Thr
20 25 30

Val Ile Lys Glu Trp Val Thr Asp Gly Lys Leu Thr Glu Phe Glu Leu
35 40 45

Glu Asp Gly Ser Tyr Thr Phe Thr Glu Ile Ser Ala Pro Asp Lys Tyr
50 55 60

Gln Val Ala Thr Ala Ile Thr Phe Glu Val Lys Ala Gly Lys Val Leu
65 70 75 80

Val Thr Gly Thr Glu Val Lys Gly Asn Thr Ile Val Gly Ser Gly Asp
85 90 95

Ile Ile Lys Leu Leu Asn Glu Gln Val Asn Lys Glu Met Gln Ser Ser
100 105 110

Asn Leu Tyr Met Ser Met Ser Ser Trp Cys Tyr Thr His Ser Leu Asp
115 120 125

Gly Ala Gly Leu Phe Leu Phe Asp His Ala Ala Glu Glu Tyr Glu His
130 135 140

Ala Lys Lys Leu Ile Ile Phe Leu Asn Glu Asn Asn Val Pro Val Gln
145 150 155 160

Leu Thr Ser Ile Ser Ala Pro Glu His Lys Phe Glu Gly Leu Thr Gln
165 170 175

Ile Phe Gln Lys Ala Tyr Glu His Glu Gln His Ile Ser Glu Ser Ile
180 185 190

Asn Asn Ile Val Asp His Ala Ile Lys Ser Lys Asp His Ala Thr Phe
195 200 205

Asn Phe Leu Gln Trp Tyr Val Ala Glu Gln His Glu Glu Glu Val Leu
210 215 220

Phe Lys Asp Ile Leu Asp Lys Ile Glu Leu Ile Gly Asn Glu Asn His
225 230 235 240

Gly Leu Tyr Leu Ala Asp Gln Tyr Val Lys Gly Ile Ala Lys Ser Arg
245 250 255

Lys Ser

<210> SEQ ID NO 24
<211> LENGTH: 260
<212> TYPE: PRT
<213> ORGANISM: Artificial Sequence
<220> FEATURE:
<223> OTHER INFORMATION: amino acid sequence of the fusion protein SaCatcher-HPF

<400> SEQUENCE: 24

Ser Thr Pro Ser Thr Lys Val Lys Phe Ser Lys Lys Ala Leu Thr Glu
1 5 10 15

Asn Gly Glu Glu Leu Lys Gly Ala Thr Ile Arg Leu Thr Lys Glu Asp
20 25 30

Gly Ser Leu Val Lys Glu Trp Val Thr Asp Gly Thr Val Lys Glu Phe
35 40 45

Glu Leu Lys Asp Gly Lys Tyr Thr Phe Thr Glu Ile Ser Ala Pro Asp
50 55 60

Lys Tyr Gln Val Ala Thr Ala Ile Thr Phe Glu Val Lys Asn Gly Lys
65 70 75 80

Val Ile Val Lys Gly Ile Glu Val Thr Gly Asn Thr Ile Val Gly Ser
85 90 95

Gly Asp Ile Ile Lys Leu Leu Asn Glu Gln Val Asn Lys Glu Met Gln
100 105 110

Ser Ser Asn Leu Tyr Met Ser Met Ser Ser Trp Cys Tyr Thr His Ser
115 120 125

Leu Asp Gly Ala Gly Leu Phe Leu Phe Asp His Ala Ala Glu Glu Tyr
130 135 140

Glu His Ala Lys Lys Leu Ile Ile Phe Leu Asn Glu Asn Asn Val Pro
145 150 155 160

Val Gln Leu Thr Ser Ile Ser Ala Pro Glu His Lys Phe Glu Gly Leu
165 170 175

Thr Gln Ile Phe Gln Lys Ala Tyr Glu His Glu Gln His Ile Ser Glu
180 185 190

Ser Ile Asn Asn Ile Val Asp His Ala Ile Lys Ser Lys Asp His Ala
195 200 205

Thr Phe Asn Phe Leu Gln Trp Tyr Val Ala Glu Gln His Glu Glu Glu
210 215 220

Val Leu Phe Lys Asp Ile Leu Asp Lys Ile Glu Leu Ile Gly Asn Glu
225 230 235 240

Asn His Gly Leu Tyr Leu Ala Asp Gln Tyr Val Lys Gly Ile Ala Lys
245 250 255

Ser Arg Lys Ser
260

<210> SEQ ID NO 25
<211> LENGTH: 272
<212> TYPE: PRT
<213> ORGANISM: Artificial Sequence
<220> FEATURE:
<223> OTHER INFORMATION: amino acid sequence of the fusion protein SdCatcher-HPF

<400> SEQUENCE: 25

Ser Gly Glu Thr Gly Gln Ser Gly Asn Thr Thr Ile Glu Glu Asp Ser
1 5 10 15

Thr Thr His Val Lys Phe Ser Lys Arg Asp Ile Asn Gly Lys Glu Leu
20 25 30

Ala Gly Ala Met Ile Glu Leu Arg Asn Leu Ser Gly Gln Thr Ile Gln
35 40 45

Ser Trp Val Ser Asp Gly Thr Val Lys Asp Phe Tyr Leu Met Pro Gly
50 55 60

Thr Tyr Gln Phe Val Glu Thr Ala Ala Pro Glu Gly Tyr Glu Leu Ala
65 70 75 80

Ala Pro Ile Thr Phe Thr Ile Asp Glu Lys Gly Gln Ile Trp Val Asp
85 90 95

Ser Thr Leu Ile Val Gly Asp Asp Pro Ile Gly Ser Gly Asp Ile Ile
100 105 110

Lys Leu Leu Asn Glu Gln Val Asn Lys Glu Met Gln Ser Ser Asn Leu
115 120 125

Tyr Met Ser Met Ser Ser Trp Cys Tyr Thr His Ser Leu Asp Gly Ala
130 135 140

Gly Leu Phe Leu Phe Asp His Ala Ala Glu Glu Tyr Glu His Ala Lys

```
145                 150                 155                 160

Lys Leu Ile Ile Phe Leu Asn Glu Asn Asn Val Pro Val Gln Leu Thr
                165                 170                 175

Ser Ile Ser Ala Pro Glu His Lys Phe Glu Gly Leu Thr Gln Ile Phe
            180                 185                 190

Gln Lys Ala Tyr Glu His Glu Gln His Ile Ser Glu Ser Ile Asn Asn
        195                 200                 205

Ile Val Asp His Ala Ile Lys Ser Lys Asp His Ala Thr Phe Asn Phe
    210                 215                 220

Leu Gln Trp Tyr Val Ala Glu Gln His Glu Glu Glu Val Leu Phe Lys
225                 230                 235                 240

Asp Ile Leu Asp Lys Ile Glu Leu Ile Gly Asn Glu Asn His Gly Leu
                245                 250                 255

Tyr Leu Ala Asp Gln Tyr Val Lys Gly Ile Ala Lys Ser Arg Lys Ser
            260                 265                 270


<210> SEQ ID NO 26
<211> LENGTH: 271
<212> TYPE: PRT
<213> ORGANISM: Artificial Sequence
<220> FEATURE:
<223> OTHER INFORMATION: amino acid sequence of the fusion protein
      AhCatcher-HPF

<400> SEQUENCE: 26

Ile Thr Asp Lys Glu Thr Gly Glu Asp Ile Tyr Leu Val Lys Asp Asp
1               5                   10                  15

Val Thr Arg Val Ser Val Lys Lys Met Asp Ile Thr Gly Gln Lys Glu
            20                  25                  30

Val Ala Gly Ala Arg Leu Leu Leu Lys Asp Lys Glu Gly Asn Val Ile
        35                  40                  45

Glu Ser Trp Met Ser Thr Thr Glu Ala Arg Val Phe Glu Gln Lys Leu
    50                  55                  60

Ile Ala Gly Glu Thr Tyr Thr Leu Thr Glu Val Thr Ala Pro Ser Gly
65                  70                  75                  80

Tyr Glu Val Ala Ala Asp Ile Thr Phe Thr Val Asn Lys Asp Gly Thr
                85                  90                  95

Val Ser Val Asp Gly Lys Ala Val Asp Gly Ser Gly Asp Ile Ile Lys
            100                 105                 110

Leu Leu Asn Glu Gln Val Asn Lys Glu Met Gln Ser Ser Asn Leu Tyr
        115                 120                 125

Met Ser Met Ser Ser Trp Cys Tyr Thr His Ser Leu Asp Gly Ala Gly
    130                 135                 140

Leu Phe Leu Phe Asp His Ala Ala Glu Glu Tyr Glu His Ala Lys Lys
145                 150                 155                 160

Leu Ile Ile Phe Leu Asn Glu Asn Asn Val Pro Val Gln Leu Thr Ser
                165                 170                 175

Ile Ser Ala Pro Glu His Lys Phe Glu Gly Leu Thr Gln Ile Phe Gln
            180                 185                 190

Lys Ala Tyr Glu His Glu Gln His Ile Ser Glu Ser Ile Asn Asn Ile
        195                 200                 205

Val Asp His Ala Ile Lys Ser Lys Asp His Ala Thr Phe Asn Phe Leu
    210                 215                 220

Gln Trp Tyr Val Ala Glu Gln His Glu Glu Glu Val Leu Phe Lys Asp
225                 230                 235                 240
```

Ile Leu Asp Lys Ile Glu Leu Ile Gly Asn Glu Asn His Gly Leu Tyr
245 250 255

Leu Ala Asp Gln Tyr Val Lys Gly Ile Ala Lys Ser Arg Lys Ser
260 265 270

<210> SEQ ID NO 27
<211> LENGTH: 266
<212> TYPE: PRT
<213> ORGANISM: Artificial Sequence
<220> FEATURE:
<223> OTHER INFORMATION: amino acid sequence of the fusion protein CpCatcher-HPF

<400> SEQUENCE: 27

Asn Asn Gln Lys Ser Glu Val Leu Lys Leu Asn Ile Ile Asp Asp Leu
1 5 10 15

Pro Lys Glu Val Leu Phe Ser Lys His Asp Ile Ala Gly Asn Glu Leu
20 25 30

Ala Gly Ala Thr Ile Glu Leu Ser Asn Lys Ala Asp Gly Lys Val Ile
35 40 45

Asp Thr Trp Val Ser Asp Gly Gln Gly Ala His Thr Phe Asn Leu Lys
50 55 60

Pro Gly Asn Tyr Val Phe Thr Glu Lys Ala Ala Pro Glu Gly Tyr Glu
65 70 75 80

Val Ala Thr Ala Ile Asn Phe Thr Val Asn Pro Asp Gly Thr Val Thr
85 90 95

Ser Asp Asp Val Gly Ser Gly Asp Ile Ile Lys Leu Leu Asn Glu Gln
100 105 110

Val Asn Lys Glu Met Gln Ser Ser Asn Leu Tyr Met Ser Met Ser Ser
115 120 125

Trp Cys Tyr Thr His Ser Leu Asp Gly Ala Gly Leu Phe Leu Phe Asp
130 135 140

His Ala Ala Glu Glu Tyr Glu His Ala Lys Lys Leu Ile Ile Phe Leu
145 150 155 160

Asn Glu Asn Asn Val Pro Val Gln Leu Thr Ser Ile Ser Ala Pro Glu
165 170 175

His Lys Phe Glu Gly Leu Thr Gln Ile Phe Gln Lys Ala Tyr Glu His
180 185 190

Glu Gln His Ile Ser Glu Ser Ile Asn Asn Ile Val Asp His Ala Ile
195 200 205

Lys Ser Lys Asp His Ala Thr Phe Asn Phe Leu Gln Trp Tyr Val Ala
210 215 220

Glu Gln His Glu Glu Glu Val Leu Phe Lys Asp Ile Leu Asp Lys Ile
225 230 235 240

Glu Leu Ile Gly Asn Glu Asn His Gly Leu Tyr Leu Ala Asp Gln Tyr
245 250 255

Val Lys Gly Ile Ala Lys Ser Arg Lys Ser
260 265

<210> SEQ ID NO 28
<211> LENGTH: 269
<212> TYPE: PRT
<213> ORGANISM: Artificial Sequence
<220> FEATURE:
<223> OTHER INFORMATION: amino acid sequence of the fusion protein RSCatcher-HPF

<400> SEQUENCE: 28

```
Thr Phe Thr Ile Asp Lys Thr Gly Lys Val Leu Val Asn Gly Glu Asp
1               5                   10                  15

Val Asn Gly Gln Val Thr Met Tyr Asp Ala Ala Leu Gly Asp Val Val
            20                  25                  30

Ile Ser Lys Arg Ala Val Asn Gly Thr Glu Glu Leu Glu Gly Ala Ser
        35                  40                  45

Leu Lys Ile Thr Asp Ala Asp Gly Lys Thr Val Ala Glu Trp Val Ser
    50                  55                  60

Asp Ser Thr Pro Lys Thr Ile Gln Leu Asp Ala Gly Thr Tyr Thr Leu
65                  70                  75                  80

Thr Glu Glu Thr Ala Pro Asp Gly Tyr Thr Val Ala Glu Ser Ile Glu
                85                  90                  95

Phe Val Val Asp Ala Ala Gly Gly Ser Gly Asp Ile Ile Lys Leu Leu
            100                 105                 110

Asn Glu Gln Val Asn Lys Glu Met Gln Ser Ser Asn Leu Tyr Met Ser
        115                 120                 125

Met Ser Ser Trp Cys Tyr Thr His Ser Leu Asp Gly Ala Gly Leu Phe
    130                 135                 140

Leu Phe Asp His Ala Ala Glu Glu Tyr Glu His Ala Lys Lys Leu Ile
145                 150                 155                 160

Ile Phe Leu Asn Glu Asn Asn Val Pro Val Gln Leu Thr Ser Ile Ser
                165                 170                 175

Ala Pro Glu His Lys Phe Glu Gly Leu Thr Gln Ile Phe Gln Lys Ala
            180                 185                 190

Tyr Glu His Glu Gln His Ile Ser Glu Ser Ile Asn Asn Ile Val Asp
        195                 200                 205

His Ala Ile Lys Ser Lys Asp His Ala Thr Phe Asn Phe Leu Gln Trp
    210                 215                 220

Tyr Val Ala Glu Gln His Glu Glu Glu Val Leu Phe Lys Asp Ile Leu
225                 230                 235                 240

Asp Lys Ile Glu Leu Ile Gly Asn Glu Asn His Gly Leu Tyr Leu Ala
                245                 250                 255

Asp Gln Tyr Val Lys Gly Ile Ala Lys Ser Arg Lys Ser
            260                 265
```

<210> SEQ ID NO 29
<211> LENGTH: 276
<212> TYPE: PRT
<213> ORGANISM: Artificial Sequence
<220> FEATURE:
<223> OTHER INFORMATION: amino acid sequence of the fusion protein ScoCatcher-HPF

<400> SEQUENCE: 29

```
Thr Val Glu Asp Thr Ser Glu Val Gln Lys Val Glu Met Lys Asp Asp
1               5                   10                  15

Val Thr Lys Val Gln Ile Ser Lys Thr Asp Ile Ser Gly Lys Glu Leu
            20                  25                  30

Pro Gly Ala Lys Leu Thr Ile Leu Asp Lys Asp Gly Lys Thr Val Glu
        35                  40                  45

Ser Trp Thr Ser Glu Glu Lys Pro His Tyr Ile Glu Met Leu Pro Ile
    50                  55                  60

Gly Glu Tyr Thr Leu Arg Glu Glu Thr Ala Pro Asp Gly Tyr Leu Val
65                  70                  75                  80

Ala Glu Asp Val Lys Phe Thr Val Lys Asp Thr Gly Glu Ile Gln Lys
                85                  90                  95
```

```
Val Val Met Lys Asp Glu Val Lys Pro Thr Ala Thr Pro Thr Gly Ser
            100                 105                 110

Gly Asp Ile Ile Lys Leu Leu Asn Glu Gln Val Asn Lys Glu Met Gln
        115                 120                 125

Ser Ser Asn Leu Tyr Met Ser Met Ser Ser Trp Cys Tyr Thr His Ser
    130                 135                 140

Leu Asp Gly Ala Gly Leu Phe Leu Phe Asp His Ala Ala Glu Glu Tyr
145                 150                 155                 160

Glu His Ala Lys Lys Leu Ile Ile Phe Leu Asn Glu Asn Asn Val Pro
                165                 170                 175

Val Gln Leu Thr Ser Ile Ser Ala Pro Glu His Lys Phe Glu Gly Leu
            180                 185                 190

Thr Gln Ile Phe Gln Lys Ala Tyr Glu His Glu Gln His Ile Ser Glu
        195                 200                 205

Ser Ile Asn Asn Ile Val Asp His Ala Ile Lys Ser Lys Asp His Ala
    210                 215                 220

Thr Phe Asn Phe Leu Gln Trp Tyr Val Ala Glu Gln His Glu Glu Glu
225                 230                 235                 240

Val Leu Phe Lys Asp Ile Leu Asp Lys Ile Glu Leu Ile Gly Asn Glu
                245                 250                 255

Asn His Gly Leu Tyr Leu Ala Asp Gln Tyr Val Lys Gly Ile Ala Lys
            260                 265                 270

Ser Arg Lys Ser
        275


<210> SEQ ID NO 30
<211> LENGTH: 271
<212> TYPE: PRT
<213> ORGANISM: Artificial Sequence
<220> FEATURE:
<223> OTHER INFORMATION: amino acid sequence of the fusion protein
      SpnCatcher-HPF

<400> SEQUENCE: 30

Gly Asn Thr Ile Val Met Val Asp Lys Leu Lys Glu Leu Pro Pro Pro
1               5                   10                  15

Pro Ser Thr Pro Pro Thr Lys Val Lys Phe Ser Lys Lys Ala Leu Thr
            20                  25                  30

Glu Asn Gly Glu Glu Leu Lys Gly Ala Thr Ile Arg Leu Thr Lys Glu
        35                  40                  45

Asp Gly Ser Leu Val Glu Glu Trp Val Thr Asp Gly Thr Val Lys Glu
    50                  55                  60

Phe Glu Leu Lys Asp Gly Lys Tyr Thr Phe Thr Glu Ile Ser Ala Pro
65                  70                  75                  80

Ala Lys Tyr Gln Val Ala Thr Ala Ile Thr Phe Glu Val Lys Asn Gly
                85                  90                  95

Lys Ala Ile Val Lys Gly Ile Glu Val Gly Ser Gly Asp Ile Ile Lys
            100                 105                 110

Leu Leu Asn Glu Gln Val Asn Lys Glu Met Gln Ser Ser Asn Leu Tyr
        115                 120                 125

Met Ser Met Ser Ser Trp Cys Tyr Thr His Ser Leu Asp Gly Ala Gly
    130                 135                 140

Leu Phe Leu Phe Asp His Ala Ala Glu Glu Tyr Glu His Ala Lys Lys
145                 150                 155                 160

Leu Ile Ile Phe Leu Asn Glu Asn Asn Val Pro Val Gln Leu Thr Ser
```

-continued

```
                165                 170                 175

Ile Ser Ala Pro Glu His Lys Phe Glu Gly Leu Thr Gln Ile Phe Gln
            180                 185                 190

Lys Ala Tyr Glu His Glu Gln His Ile Ser Glu Ser Ile Asn Asn Ile
        195                 200                 205

Val Asp His Ala Ile Lys Ser Lys Asp His Ala Thr Phe Asn Phe Leu
    210                 215                 220

Gln Trp Tyr Val Ala Glu Gln His Glu Glu Val Leu Phe Lys Asp
225                 230                 235                 240

Ile Leu Asp Lys Ile Glu Leu Ile Gly Asn Glu Asn His Gly Leu Tyr
                245                 250                 255

Leu Ala Asp Gln Tyr Val Lys Gly Ile Ala Lys Ser Arg Lys Ser
            260                 265                 270


<210> SEQ ID NO 31
<211> LENGTH: 267
<212> TYPE: PRT
<213> ORGANISM: Artificial Sequence
<220> FEATURE:
<223> OTHER INFORMATION: amino acid sequence of the fusion protein
      GvTag-GFP

<400> SEQUENCE: 31

Met Val Asp Lys Leu Lys Glu Val Pro Thr Ser Thr Lys Val Lys Phe
1               5                   10                  15

Ser Lys Lys Ala Leu Thr Glu Asn Gly Glu Asp Leu Lys Gly Ala Thr
            20                  25                  30

Ile Gln Leu Thr Lys Ala Asp Gly Ser Leu Val Lys Lys Trp Val Thr
        35                  40                  45

Asp Gly Thr Val Thr Glu Phe Glu Leu Lys Asp Gly Lys Tyr Thr Phe
    50                  55                  60

Thr Glu Thr Ser Ala Pro Ala Lys Tyr Gln Val Ala Thr Ala Ile Thr
65                  70                  75                  80

Phe Glu Val Lys Asn Gly Lys Ala Ile Val Lys Gly Ile Ala Val Thr
                85                  90                  95

Gly Asn Thr Ile Val Gly Ser Gly Asp Ile Ile Lys Leu Leu Asn Glu
            100                 105                 110

Gln Val Asn Lys Glu Met Gln Ser Ser Asn Leu Tyr Met Ser Met Ser
        115                 120                 125

Ser Trp Cys Tyr Thr His Ser Leu Asp Gly Ala Gly Leu Phe Leu Phe
    130                 135                 140

Asp His Ala Ala Glu Glu Tyr Glu His Ala Lys Lys Leu Ile Ile Phe
145                 150                 155                 160

Leu Asn Glu Asn Asn Val Pro Val Gln Leu Thr Ser Ile Ser Ala Pro
                165                 170                 175

Glu His Lys Phe Glu Gly Leu Thr Gln Ile Phe Gln Lys Ala Tyr Glu
            180                 185                 190

His Glu Gln His Ile Ser Glu Ser Ile Asn Asn Ile Val Asp His Ala
        195                 200                 205

Ile Lys Ser Lys Asp His Ala Thr Phe Asn Phe Leu Gln Trp Tyr Val
    210                 215                 220

Ala Glu Gln His Glu Glu Glu Val Leu Phe Lys Asp Ile Leu Asp Lys
225                 230                 235                 240

Ile Glu Leu Ile Gly Asn Glu Asn His Gly Leu Tyr Leu Ala Asp Gln
                245                 250                 255
```

```
Tyr Val Lys Gly Ile Ala Lys Ser Arg Lys Ser
            260                 265


<210> SEQ ID NO 32
<211> LENGTH: 265
<212> TYPE: PRT
<213> ORGANISM: Artificial Sequence
<220> FEATURE:
<223> OTHER INFORMATION: amino acid sequence of the fusion protein
      GbTag-GFP

<400> SEQUENCE: 32

Val Val Thr Asp Gly Tyr Ser Ser His Asp Ile Asn Ile Ser Lys Ala
1               5                   10                  15

Asp Ile Asp Gly Asn Glu Ile Ala Gly Ala Lys Ile Val Leu Thr Asp
            20                  25                  30

Lys Ala Gly Lys Gln Ile Asp Ser Trp Thr Ser Thr Lys Glu Leu His
        35                  40                  45

Lys Val Ser Leu Lys Pro Gly Thr Tyr Ile Phe Lys Glu Thr Leu Ala
    50                  55                  60

Pro Glu Gly Phe Glu Val Val Thr Asp Ile Thr Phe Thr Val Asn Val
65                  70                  75                  80

Asp Gly Thr Ile Thr Val Asn Asp Lys Gln Ala Lys Val Asn Asn Asp
                85                  90                  95

Gly Val Leu Gly Ser Gly Asp Ile Ile Lys Leu Leu Asn Glu Gln Val
            100                 105                 110

Asn Lys Glu Met Gln Ser Ser Asn Leu Tyr Met Ser Met Ser Ser Trp
        115                 120                 125

Cys Tyr Thr His Ser Leu Asp Gly Ala Gly Leu Phe Leu Phe Asp His
    130                 135                 140

Ala Ala Glu Glu Tyr Glu His Ala Lys Lys Leu Ile Ile Phe Leu Asn
145                 150                 155                 160

Glu Asn Asn Val Pro Val Gln Leu Thr Ser Ile Ser Ala Pro Glu His
                165                 170                 175

Lys Phe Glu Gly Leu Thr Gln Ile Phe Gln Lys Ala Tyr Glu His Glu
            180                 185                 190

Gln His Ile Ser Glu Ser Ile Asn Asn Ile Val Asp His Ala Ile Lys
        195                 200                 205

Ser Lys Asp His Ala Thr Phe Asn Phe Leu Gln Trp Tyr Val Ala Glu
    210                 215                 220

Gln His Glu Glu Glu Val Leu Phe Lys Asp Ile Leu Asp Lys Ile Glu
225                 230                 235                 240

Leu Ile Gly Asn Glu Asn His Gly Leu Tyr Leu Ala Asp Gln Tyr Val
                245                 250                 255

Lys Gly Ile Ala Lys Ser Arg Lys Ser
            260                 265


<210> SEQ ID NO 33
<211> LENGTH: 258
<212> TYPE: PRT
<213> ORGANISM: Artificial Sequence
<220> FEATURE:
<223> OTHER INFORMATION: amino acid sequence of the fusion protein
      PsTag-GFP

<400> SEQUENCE: 33

Glu Lys Thr Lys Val Lys Phe Ser Lys Lys Ala Leu Thr Ala Asn Gly
1               5                   10                  15
```

Glu Glu Leu Lys Gly Ala Thr Ile Lys Leu Thr Lys Glu Asn Gly Thr
20 25 30

Val Ile Lys Glu Trp Val Thr Asp Gly Lys Leu Thr Glu Phe Glu Leu
35 40 45

Glu Asp Gly Ser Tyr Thr Phe Thr Glu Ile Ser Ala Pro Asp Lys Tyr
50 55 60

Gln Val Ala Thr Ala Ile Thr Phe Glu Val Lys Ala Gly Lys Val Leu
65 70 75 80

Val Thr Gly Thr Glu Val Lys Gly Asn Thr Ile Val Gly Ser Gly Asp
85 90 95

Ile Ile Lys Leu Leu Asn Glu Gln Val Asn Lys Glu Met Gln Ser Ser
100 105 110

Asn Leu Tyr Met Ser Met Ser Ser Trp Cys Tyr Thr His Ser Leu Asp
115 120 125

Gly Ala Gly Leu Phe Leu Phe Asp His Ala Ala Glu Glu Tyr Glu His
130 135 140

Ala Lys Lys Leu Ile Ile Phe Leu Asn Glu Asn Asn Val Pro Val Gln
145 150 155 160

Leu Thr Ser Ile Ser Ala Pro Glu His Lys Phe Glu Gly Leu Thr Gln
165 170 175

Ile Phe Gln Lys Ala Tyr Glu His Glu Gln His Ile Ser Glu Ser Ile
180 185 190

Asn Asn Ile Val Asp His Ala Ile Lys Ser Lys Asp His Ala Thr Phe
195 200 205

Asn Phe Leu Gln Trp Tyr Val Ala Glu Gln His Glu Glu Glu Val Leu
210 215 220

Phe Lys Asp Ile Leu Asp Lys Ile Glu Leu Ile Gly Asn Glu Asn His
225 230 235 240

Gly Leu Tyr Leu Ala Asp Gln Tyr Val Lys Gly Ile Ala Lys Ser Arg
245 250 255

Lys Ser

<210> SEQ ID NO 34
<211> LENGTH: 260
<212> TYPE: PRT
<213> ORGANISM: Artificial Sequence
<220> FEATURE:
<223> OTHER INFORMATION: amino acid sequence of the fusion protein SaTag-GFP

<400> SEQUENCE: 34

Ser Thr Pro Ser Thr Lys Val Lys Phe Ser Lys Lys Ala Leu Thr Glu
1 5 10 15

Asn Gly Glu Glu Leu Lys Gly Ala Thr Ile Arg Leu Thr Lys Glu Asp
20 25 30

Gly Ser Leu Val Lys Glu Trp Val Thr Asp Gly Thr Val Lys Glu Phe
35 40 45

Glu Leu Lys Asp Gly Lys Tyr Thr Phe Thr Glu Ile Ser Ala Pro Asp
50 55 60

Lys Tyr Gln Val Ala Thr Ala Ile Thr Phe Glu Val Lys Asn Gly Lys
65 70 75 80

Val Ile Val Lys Gly Ile Glu Val Thr Gly Asn Thr Ile Val Gly Ser
85 90 95

Gly Asp Ile Ile Lys Leu Leu Asn Glu Gln Val Asn Lys Glu Met Gln
100 105 110

-continued

Ser Ser Asn Leu Tyr Met Ser Met Ser Ser Trp Cys Tyr Thr His Ser
115 120 125

Leu Asp Gly Ala Gly Leu Phe Leu Phe Asp His Ala Ala Glu Glu Tyr
130 135 140

Glu His Ala Lys Lys Leu Ile Ile Phe Leu Asn Glu Asn Asn Val Pro
145 150 155 160

Val Gln Leu Thr Ser Ile Ser Ala Pro Glu His Lys Phe Glu Gly Leu
165 170 175

Thr Gln Ile Phe Gln Lys Ala Tyr Glu His Glu Gln His Ile Ser Glu
180 185 190

Ser Ile Asn Asn Ile Val Asp His Ala Ile Lys Ser Lys Asp His Ala
195 200 205

Thr Phe Asn Phe Leu Gln Trp Tyr Val Ala Glu Gln His Glu Glu Glu
210 215 220

Val Leu Phe Lys Asp Ile Leu Asp Lys Ile Glu Leu Ile Gly Asn Glu
225 230 235 240

Asn His Gly Leu Tyr Leu Ala Asp Gln Tyr Val Lys Gly Ile Ala Lys
245 250 255

Ser Arg Lys Ser
260

<210> SEQ ID NO 35
<211> LENGTH: 272
<212> TYPE: PRT
<213> ORGANISM: Artificial Sequence
<220> FEATURE:
<223> OTHER INFORMATION: amino acid sequence of the fusion protein SdTag-GFP

<400> SEQUENCE: 35

Ser Gly Glu Thr Gly Gln Ser Gly Asn Thr Thr Ile Glu Glu Asp Ser
1 5 10 15

Thr Thr His Val Lys Phe Ser Lys Arg Asp Ile Asn Gly Lys Glu Leu
20 25 30

Ala Gly Ala Met Ile Glu Leu Arg Asn Leu Ser Gly Gln Thr Ile Gln
35 40 45

Ser Trp Val Ser Asp Gly Thr Val Lys Asp Phe Tyr Leu Met Pro Gly
50 55 60

Thr Tyr Gln Phe Val Glu Thr Ala Ala Pro Glu Gly Tyr Glu Leu Ala
65 70 75 80

Ala Pro Ile Thr Phe Thr Ile Asp Glu Lys Gly Gln Ile Trp Val Asp
85 90 95

Ser Thr Leu Ile Val Gly Asp Asp Pro Ile Gly Ser Gly Asp Ile Ile
100 105 110

Lys Leu Leu Asn Glu Gln Val Asn Lys Glu Met Gln Ser Ser Asn Leu
115 120 125

Tyr Met Ser Met Ser Ser Trp Cys Tyr Thr His Ser Leu Asp Gly Ala
130 135 140

Gly Leu Phe Leu Phe Asp His Ala Ala Glu Glu Tyr Glu His Ala Lys
145 150 155 160

Lys Leu Ile Ile Phe Leu Asn Glu Asn Asn Val Pro Val Gln Leu Thr
165 170 175

Ser Ile Ser Ala Pro Glu His Lys Phe Glu Gly Leu Thr Gln Ile Phe
180 185 190

Gln Lys Ala Tyr Glu His Glu Gln His Ile Ser Glu Ser Ile Asn Asn
195 200 205

```
Ile Val Asp His Ala Ile Lys Ser Lys Asp His Ala Thr Phe Asn Phe
    210                 215                 220

Leu Gln Trp Tyr Val Ala Glu Gln His Glu Glu Glu Val Leu Phe Lys
225                 230                 235                 240

Asp Ile Leu Asp Lys Ile Glu Leu Ile Gly Asn Glu Asn His Gly Leu
                245                 250                 255

Tyr Leu Ala Asp Gln Tyr Val Lys Gly Ile Ala Lys Ser Arg Lys Ser
            260                 265                 270


<210> SEQ ID NO 36
<211> LENGTH: 271
<212> TYPE: PRT
<213> ORGANISM: Artificial Sequence
<220> FEATURE:
<223> OTHER INFORMATION: amino acid sequence of the fusion protein
      AhTag-GFP

<400> SEQUENCE: 36

Ile Thr Asp Lys Glu Thr Gly Glu Asp Ile Tyr Leu Val Lys Asp Asp
1               5                   10                  15

Val Thr Arg Val Ser Val Lys Lys Met Asp Ile Thr Gly Gln Lys Glu
            20                  25                  30

Val Ala Gly Ala Arg Leu Leu Leu Lys Asp Lys Glu Gly Asn Val Ile
        35                  40                  45

Glu Ser Trp Met Ser Thr Thr Glu Ala Arg Val Phe Glu Gln Lys Leu
    50                  55                  60

Ile Ala Gly Glu Thr Tyr Thr Leu Thr Glu Val Thr Ala Pro Ser Gly
65                  70                  75                  80

Tyr Glu Val Ala Ala Asp Ile Thr Phe Thr Val Asn Lys Asp Gly Thr
                85                  90                  95

Val Ser Val Asp Gly Lys Ala Val Asp Gly Ser Gly Asp Ile Ile Lys
            100                 105                 110

Leu Leu Asn Glu Gln Val Asn Lys Glu Met Gln Ser Ser Asn Leu Tyr
        115                 120                 125

Met Ser Met Ser Ser Trp Cys Tyr Thr His Ser Leu Asp Gly Ala Gly
    130                 135                 140

Leu Phe Leu Phe Asp His Ala Ala Glu Glu Tyr Glu His Ala Lys Lys
145                 150                 155                 160

Leu Ile Ile Phe Leu Asn Glu Asn Asn Val Pro Val Gln Leu Thr Ser
                165                 170                 175

Ile Ser Ala Pro Glu His Lys Phe Glu Gly Leu Thr Gln Ile Phe Gln
            180                 185                 190

Lys Ala Tyr Glu His Glu Gln His Ile Ser Glu Ser Ile Asn Asn Ile
        195                 200                 205

Val Asp His Ala Ile Lys Ser Lys Asp His Ala Thr Phe Asn Phe Leu
    210                 215                 220

Gln Trp Tyr Val Ala Glu Gln His Glu Glu Glu Val Leu Phe Lys Asp
225                 230                 235                 240

Ile Leu Asp Lys Ile Glu Leu Ile Gly Asn Glu Asn His Gly Leu Tyr
                245                 250                 255

Leu Ala Asp Gln Tyr Val Lys Gly Ile Ala Lys Ser Arg Lys Ser
            260                 265                 270


<210> SEQ ID NO 37
<211> LENGTH: 266
<212> TYPE: PRT
```

<213> ORGANISM: Artificial Sequence
<220> FEATURE:
<223> OTHER INFORMATION: amino acid sequence of the fusion protein
CpTag-GFP

<400> SEQUENCE: 37

```
Asn Asn Gln Lys Ser Glu Val Leu Lys Leu Asn Ile Ile Asp Asp Leu
1               5                   10                  15

Pro Lys Glu Val Leu Phe Ser Lys His Asp Ile Ala Gly Asn Glu Leu
            20                  25                  30

Ala Gly Ala Thr Ile Glu Leu Ser Asn Lys Ala Asp Gly Lys Val Ile
        35                  40                  45

Asp Thr Trp Val Ser Asp Gly Gln Gly Ala His Thr Phe Asn Leu Lys
    50                  55                  60

Pro Gly Asn Tyr Val Phe Thr Glu Lys Ala Ala Pro Glu Gly Tyr Glu
65                  70                  75                  80

Val Ala Thr Ala Ile Asn Phe Thr Val Asn Pro Asp Gly Thr Val Thr
                85                  90                  95

Ser Asp Asp Val Gly Ser Gly Asp Ile Ile Lys Leu Leu Asn Glu Gln
            100                 105                 110

Val Asn Lys Glu Met Gln Ser Ser Asn Leu Tyr Met Ser Met Ser Ser
        115                 120                 125

Trp Cys Tyr Thr His Ser Leu Asp Gly Ala Gly Leu Phe Leu Phe Asp
    130                 135                 140

His Ala Ala Glu Glu Tyr Glu His Ala Lys Lys Leu Ile Ile Phe Leu
145                 150                 155                 160

Asn Glu Asn Asn Val Pro Val Gln Leu Thr Ser Ile Ser Ala Pro Glu
                165                 170                 175

His Lys Phe Glu Gly Leu Thr Gln Ile Phe Gln Lys Ala Tyr Glu His
            180                 185                 190

Glu Gln His Ile Ser Glu Ser Ile Asn Asn Ile Val Asp His Ala Ile
        195                 200                 205

Lys Ser Lys Asp His Ala Thr Phe Asn Phe Leu Gln Trp Tyr Val Ala
    210                 215                 220

Glu Gln His Glu Glu Glu Val Leu Phe Lys Asp Ile Leu Asp Lys Ile
225                 230                 235                 240

Glu Leu Ile Gly Asn Glu Asn His Gly Leu Tyr Leu Ala Asp Gln Tyr
                245                 250                 255

Val Lys Gly Ile Ala Lys Ser Arg Lys Ser
            260                 265
```

<210> SEQ ID NO 38
<211> LENGTH: 269
<212> TYPE: PRT
<213> ORGANISM: Artificial Sequence
<220> FEATURE:
<223> OTHER INFORMATION: amino acid sequence of the fusion protein
RSTag-GFP

<400> SEQUENCE: 38

```
Thr Phe Thr Ile Asp Lys Thr Gly Lys Val Leu Val Asn Gly Glu Asp
1               5                   10                  15

Val Asn Gly Gln Val Thr Met Tyr Asp Ala Ala Leu Gly Asp Val Val
            20                  25                  30

Ile Ser Lys Arg Ala Val Asn Gly Thr Glu Glu Leu Glu Gly Ala Ser
        35                  40                  45

Leu Lys Ile Thr Asp Ala Asp Gly Lys Thr Val Ala Glu Trp Val Ser
```

```
    50                  55                  60

Asp Ser Thr Pro Lys Thr Ile Gln Leu Asp Ala Gly Thr Tyr Thr Leu
65                  70                  75                  80

Thr Glu Glu Thr Ala Pro Asp Gly Tyr Thr Val Ala Glu Ser Ile Glu
                85                  90                  95

Phe Val Val Asp Ala Ala Gly Gly Ser Gly Asp Ile Ile Lys Leu Leu
            100                 105                 110

Asn Glu Gln Val Asn Lys Glu Met Gln Ser Ser Asn Leu Tyr Met Ser
        115                 120                 125

Met Ser Ser Trp Cys Tyr Thr His Ser Leu Asp Gly Ala Gly Leu Phe
    130                 135                 140

Leu Phe Asp His Ala Ala Glu Glu Tyr Glu His Ala Lys Lys Leu Ile
145                 150                 155                 160

Ile Phe Leu Asn Glu Asn Asn Val Pro Val Gln Leu Thr Ser Ile Ser
                165                 170                 175

Ala Pro Glu His Lys Phe Glu Gly Leu Thr Gln Ile Phe Gln Lys Ala
            180                 185                 190

Tyr Glu His Glu Gln His Ile Ser Glu Ser Ile Asn Asn Ile Val Asp
        195                 200                 205

His Ala Ile Lys Ser Lys Asp His Ala Thr Phe Asn Phe Leu Gln Trp
    210                 215                 220

Tyr Val Ala Glu Gln His Glu Glu Glu Val Leu Phe Lys Asp Ile Leu
225                 230                 235                 240

Asp Lys Ile Glu Leu Ile Gly Asn Glu Asn His Gly Leu Tyr Leu Ala
                245                 250                 255

Asp Gln Tyr Val Lys Gly Ile Ala Lys Ser Arg Lys Ser
            260                 265


<210> SEQ ID NO 39
<211> LENGTH: 276
<212> TYPE: PRT
<213> ORGANISM: Artificial Sequence
<220> FEATURE:
<223> OTHER INFORMATION: amino acid sequence of the fusion protein
      ScoTag-GFP

<400> SEQUENCE: 39

Thr Val Glu Asp Thr Ser Glu Val Gln Lys Val Glu Met Lys Asp Asp
1               5                   10                  15

Val Thr Lys Val Gln Ile Ser Lys Thr Asp Ile Ser Gly Lys Glu Leu
            20                  25                  30

Pro Gly Ala Lys Leu Thr Ile Leu Asp Lys Asp Gly Lys Thr Val Glu
        35                  40                  45

Ser Trp Thr Ser Glu Glu Lys Pro His Tyr Ile Glu Met Leu Pro Ile
    50                  55                  60

Gly Glu Tyr Thr Leu Arg Glu Glu Thr Ala Pro Asp Gly Tyr Leu Val
65                  70                  75                  80

Ala Glu Asp Val Lys Phe Thr Val Lys Asp Thr Gly Glu Ile Gln Lys
                85                  90                  95

Val Val Met Lys Asp Glu Val Lys Pro Thr Ala Thr Pro Thr Gly Ser
            100                 105                 110

Gly Asp Ile Ile Lys Leu Leu Asn Glu Gln Val Asn Lys Glu Met Gln
        115                 120                 125

Ser Ser Asn Leu Tyr Met Ser Met Ser Ser Trp Cys Tyr Thr His Ser
    130                 135                 140
```

```
Leu Asp Gly Ala Gly Leu Phe Leu Phe Asp His Ala Ala Glu Glu Tyr
145                 150                 155                 160

Glu His Ala Lys Lys Leu Ile Ile Phe Leu Asn Glu Asn Asn Val Pro
                165                 170                 175

Val Gln Leu Thr Ser Ile Ser Ala Pro Glu His Lys Phe Glu Gly Leu
            180                 185                 190

Thr Gln Ile Phe Gln Lys Ala Tyr Glu His Glu Gln His Ile Ser Glu
        195                 200                 205

Ser Ile Asn Asn Ile Val Asp His Ala Ile Lys Ser Lys Asp His Ala
    210                 215                 220

Thr Phe Asn Phe Leu Gln Trp Tyr Val Ala Glu Gln His Glu Glu Glu
225                 230                 235                 240

Val Leu Phe Lys Asp Ile Leu Asp Lys Ile Glu Leu Ile Gly Asn Glu
                245                 250                 255

Asn His Gly Leu Tyr Leu Ala Asp Gln Tyr Val Lys Gly Ile Ala Lys
            260                 265                 270

Ser Arg Lys Ser
        275


<210> SEQ ID NO 40
<211> LENGTH: 271
<212> TYPE: PRT
<213> ORGANISM: Artificial Sequence
<220> FEATURE:
<223> OTHER INFORMATION: amino acid sequence of the fusion protein
      SpnTag-GFP

<400> SEQUENCE: 40

Gly Asn Thr Ile Val Met Val Asp Lys Leu Lys Glu Leu Pro Pro Pro
1               5                   10                  15

Pro Ser Thr Pro Pro Thr Lys Val Lys Phe Ser Lys Lys Ala Leu Thr
            20                  25                  30

Glu Asn Gly Glu Glu Leu Lys Gly Ala Thr Ile Arg Leu Thr Lys Glu
        35                  40                  45

Asp Gly Ser Leu Val Glu Glu Trp Val Thr Asp Gly Thr Val Lys Glu
    50                  55                  60

Phe Glu Leu Lys Asp Gly Lys Tyr Thr Phe Thr Glu Ile Ser Ala Pro
65                  70                  75                  80

Ala Lys Tyr Gln Val Ala Thr Ala Ile Thr Phe Glu Val Lys Asn Gly
                85                  90                  95

Lys Ala Ile Val Lys Gly Ile Glu Val Gly Ser Gly Asp Ile Ile Lys
            100                 105                 110

Leu Leu Asn Glu Gln Val Asn Lys Glu Met Gln Ser Ser Asn Leu Tyr
        115                 120                 125

Met Ser Met Ser Ser Trp Cys Tyr Thr His Ser Leu Asp Gly Ala Gly
    130                 135                 140

Leu Phe Leu Phe Asp His Ala Ala Glu Glu Tyr Glu His Ala Lys Lys
145                 150                 155                 160

Leu Ile Ile Phe Leu Asn Glu Asn Asn Val Pro Val Gln Leu Thr Ser
                165                 170                 175

Ile Ser Ala Pro Glu His Lys Phe Glu Gly Leu Thr Gln Ile Phe Gln
            180                 185                 190

Lys Ala Tyr Glu His Glu Gln His Ile Ser Glu Ser Ile Asn Asn Ile
        195                 200                 205

Val Asp His Ala Ile Lys Ser Lys Asp His Ala Thr Phe Asn Phe Leu
    210                 215                 220
```

Gln Trp Tyr Val Ala Glu Gln His Glu Glu Glu Val Leu Phe Lys Asp
225 230 235 240

Ile Leu Asp Lys Ile Glu Leu Ile Gly Asn Glu Asn His Gly Leu Tyr
245 250 255

Leu Ala Asp Gln Tyr Val Lys Gly Ile Ala Lys Ser Arg Lys Ser
260 265 270

<210> SEQ ID NO 41
<211> LENGTH: 278
<212> TYPE: PRT
<213> ORGANISM: Artificial Sequence
<220> FEATURE:
<223> OTHER INFORMATION: amino acid sequence of the fusion protein SP-GvTag-RBD-His

<400> SEQUENCE: 41

Met Gly Ile Leu Pro Ser Pro Gly Met Pro Ala Leu Leu Ser Leu Val
1 5 10 15

Ser Leu Leu Ser Val Leu Leu Met Gly Cys Val Ala Gly Ser Gly Asn
20 25 30

Thr Ile Val Met Val Asp Lys Leu Lys Glu Val Pro Thr Pro Gly Ser
35 40 45

Gly Arg Val Gln Pro Thr Glu Ser Ile Val Arg Phe Pro Asn Ile Thr
50 55 60

Asn Leu Cys Pro Phe Gly Glu Val Phe Asn Ala Thr Arg Phe Ala Ser
65 70 75 80

Val Tyr Ala Trp Asn Arg Lys Arg Ile Ser Asn Cys Val Ala Asp Tyr
85 90 95

Ser Val Leu Tyr Asn Ser Ala Ser Phe Ser Thr Phe Lys Cys Tyr Gly
100 105 110

Val Ser Pro Thr Lys Leu Asn Asp Leu Cys Phe Thr Asn Val Tyr Ala
115 120 125

Asp Ser Phe Val Ile Arg Gly Asp Glu Val Arg Gln Ile Ala Pro Gly
130 135 140

Gln Thr Gly Lys Ile Ala Asp Tyr Asn Tyr Lys Leu Pro Asp Asp Phe
145 150 155 160

Thr Gly Cys Val Ile Ala Trp Asn Ser Asn Asn Leu Asp Ser Lys Val
165 170 175

Gly Gly Asn Tyr Asn Tyr Leu Tyr Arg Leu Phe Arg Lys Ser Asn Leu
180 185 190

Lys Pro Phe Glu Arg Asp Ile Ser Thr Glu Ile Tyr Gln Ala Gly Ser
195 200 205

Thr Pro Cys Asn Gly Val Glu Gly Phe Asn Cys Tyr Phe Pro Leu Gln
210 215 220

Ser Tyr Gly Phe Gln Pro Thr Asn Gly Val Gly Tyr Gln Pro Tyr Arg
225 230 235 240

Val Val Val Leu Ser Phe Glu Leu Leu His Ala Pro Ala Thr Val Cys
245 250 255

Gly Pro Lys Lys Ser Thr Asn Leu Val Lys Asn Lys Cys Val Asn Phe
260 265 270

His His His His His His
275

<210> SEQ ID NO 42
<211> LENGTH: 276
<212> TYPE: PRT

<213> ORGANISM: Artificial Sequence
<220> FEATURE:
<223> OTHER INFORMATION: amino acid sequence of the fusion protein
SP-PsTag-RBD-His

<400> SEQUENCE: 42

```
Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Gly Ser Gly Asn
            20                  25                  30

Thr Ile Val Met Val Asp Lys Leu Lys Lys Thr Pro Gly Ser Gly Arg
        35                  40                  45

Val Gln Pro Thr Glu Ser Ile Val Arg Phe Pro Asn Ile Thr Asn Leu
    50                  55                  60

Cys Pro Phe Gly Glu Val Phe Asn Ala Thr Arg Phe Ala Ser Val Tyr
65                  70                  75                  80

Ala Trp Asn Arg Lys Arg Ile Ser Asn Cys Val Ala Asp Tyr Ser Val
                85                  90                  95

Leu Tyr Asn Ser Ala Ser Phe Ser Thr Phe Lys Cys Tyr Gly Val Ser
            100                 105                 110

Pro Thr Lys Leu Asn Asp Leu Cys Phe Thr Asn Val Tyr Ala Asp Ser
        115                 120                 125

Phe Val Ile Arg Gly Asp Glu Val Arg Gln Ile Ala Pro Gly Gln Thr
    130                 135                 140

Gly Lys Ile Ala Asp Tyr Asn Tyr Lys Leu Pro Asp Asp Phe Thr Gly
145                 150                 155                 160

Cys Val Ile Ala Trp Asn Ser Asn Asn Leu Asp Ser Lys Val Gly Gly
                165                 170                 175

Asn Tyr Asn Tyr Leu Tyr Arg Leu Phe Arg Lys Ser Asn Leu Lys Pro
            180                 185                 190

Phe Glu Arg Asp Ile Ser Thr Glu Ile Tyr Gln Ala Gly Ser Thr Pro
        195                 200                 205

Cys Asn Gly Val Glu Gly Phe Asn Cys Tyr Phe Pro Leu Gln Ser Tyr
    210                 215                 220

Gly Phe Gln Pro Thr Asn Gly Val Gly Tyr Gln Pro Tyr Arg Val Val
225                 230                 235                 240

Val Leu Ser Phe Glu Leu Leu His Ala Pro Ala Thr Val Cys Gly Pro
                245                 250                 255

Lys Lys Ser Thr Asn Leu Val Lys Asn Lys Cys Val Asn Phe His His
            260                 265                 270

His His His His
        275
```

<210> SEQ ID NO 43
<211> LENGTH: 278
<212> TYPE: PRT
<213> ORGANISM: Artificial Sequence
<220> FEATURE:
<223> OTHER INFORMATION: amino acid sequence of the fusion protein
SP-SaTag-RBD-His

<400> SEQUENCE: 43

```
Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Gly Ser Gly Asn
            20                  25                  30

Thr Ile Val Met Val Asp Lys Leu Lys Glu Leu Pro Pro Pro Gly Ser
```

```
        35                  40                  45

Gly Arg Val Gln Pro Thr Glu Ser Ile Val Arg Phe Pro Asn Ile Thr
    50                  55                  60

Asn Leu Cys Pro Phe Gly Glu Val Phe Asn Ala Thr Arg Phe Ala Ser
65                  70                  75                  80

Val Tyr Ala Trp Asn Arg Lys Arg Ile Ser Asn Cys Val Ala Asp Tyr
                85                  90                  95

Ser Val Leu Tyr Asn Ser Ala Ser Phe Ser Thr Phe Lys Cys Tyr Gly
            100                 105                 110

Val Ser Pro Thr Lys Leu Asn Asp Leu Cys Phe Thr Asn Val Tyr Ala
        115                 120                 125

Asp Ser Phe Val Ile Arg Gly Asp Glu Val Arg Gln Ile Ala Pro Gly
    130                 135                 140

Gln Thr Gly Lys Ile Ala Asp Tyr Asn Tyr Lys Leu Pro Asp Asp Phe
145                 150                 155                 160

Thr Gly Cys Val Ile Ala Trp Asn Ser Asn Asn Leu Asp Ser Lys Val
                165                 170                 175

Gly Gly Asn Tyr Asn Tyr Leu Tyr Arg Leu Phe Arg Lys Ser Asn Leu
            180                 185                 190

Lys Pro Phe Glu Arg Asp Ile Ser Thr Glu Ile Tyr Gln Ala Gly Ser
        195                 200                 205

Thr Pro Cys Asn Gly Val Glu Gly Phe Asn Cys Tyr Phe Pro Leu Gln
    210                 215                 220

Ser Tyr Gly Phe Gln Pro Thr Asn Gly Val Gly Tyr Gln Pro Tyr Arg
225                 230                 235                 240

Val Val Val Leu Ser Phe Glu Leu Leu His Ala Pro Ala Thr Val Cys
                245                 250                 255

Gly Pro Lys Lys Ser Thr Asn Leu Val Lys Asn Lys Cys Val Asn Phe
            260                 265                 270

His His His His His His
        275


<210> SEQ ID NO 44
<211> LENGTH: 18
<212> TYPE: PRT
<213> ORGANISM: Artificial Sequence
<220> FEATURE:
<223> OTHER INFORMATION: amino acid sequence of the peptide tag GvTag001

<400> SEQUENCE: 44

Arg Val Gly Asn Thr Ile Val Met Val Asp Lys Leu Lys Glu Val Pro
1               5                   10                  15

Thr Pro


<210> SEQ ID NO 45
<211> LENGTH: 19
<212> TYPE: PRT
<213> ORGANISM: Artificial Sequence
<220> FEATURE:
<223> OTHER INFORMATION: amino acid sequence of the peptide tag GvTag002

<400> SEQUENCE: 45

Lys Lys Val Gly Asn Thr Ile Val Met Val Asp Lys Leu Lys Glu Val
1               5                   10                  15

Pro Thr Pro


<210> SEQ ID NO 46
```

<211> LENGTH: 18
<212> TYPE: PRT
<213> ORGANISM: Artificial Sequence
<220> FEATURE:
<223> OTHER INFORMATION: amino acid sequence of the peptide tag GvTagOpti

<400> SEQUENCE: 46

Lys Val Gly Asn Thr Ile Val Met Val Asp Lys Leu Lys Glu Val Pro
1 5 10 15

Thr Pro

<210> SEQ ID NO 47
<211> LENGTH: 281
<212> TYPE: PRT
<213> ORGANISM: Artificial Sequence
<220> FEATURE:
<223> OTHER INFORMATION: amino acid sequence of the fusion protein Sp-GvTag001-RBD-His

<400> SEQUENCE: 47

Met Gly Ile Leu Pro Ser Pro Gly Met Pro Ala Leu Leu Ser Leu Val
1 5 10 15

Ser Leu Leu Ser Val Leu Leu Met Gly Cys Val Ala Gly Ser Gly Arg
20 25 30

Val Gly Asn Thr Ile Val Met Val Asp Lys Leu Lys Glu Val Pro Thr
35 40 45

Pro Gly Ser Gly Arg Val Gln Pro Thr Glu Ser Ile Val Arg Phe Pro
50 55 60

Asn Ile Thr Asn Leu Cys Pro Phe Gly Glu Val Phe Asn Ala Thr Arg
65 70 75 80

Phe Ala Ser Val Tyr Ala Trp Asn Arg Lys Arg Ile Ser Asn Cys Val
85 90 95

Ala Asp Tyr Ser Val Leu Tyr Asn Ser Ala Ser Phe Ser Thr Phe Lys
100 105 110

Cys Tyr Gly Val Ser Pro Thr Lys Leu Asn Asp Leu Cys Phe Thr Asn
115 120 125

Val Tyr Ala Asp Ser Phe Val Ile Arg Gly Asp Glu Val Arg Gln Ile
130 135 140

Ala Pro Gly Gln Thr Gly Lys Ile Ala Asp Tyr Asn Tyr Lys Leu Pro
145 150 155 160

Asp Asp Phe Thr Gly Cys Val Ile Ala Trp Asn Ser Asn Asn Leu Asp
165 170 175

Ser Lys Val Gly Gly Asn Tyr Asn Tyr Leu Tyr Arg Leu Phe Arg Lys
180 185 190

Ser Asn Leu Lys Pro Phe Glu Arg Asp Ile Ser Thr Glu Ile Tyr Gln
195 200 205

Ala Gly Ser Thr Pro Cys Asn Gly Val Glu Gly Phe Asn Cys Tyr Phe
210 215 220

Pro Leu Gln Ser Tyr Gly Phe Gln Pro Thr Asn Gly Val Gly Tyr Gln
225 230 235 240

Pro Tyr Arg Val Val Val Leu Ser Phe Glu Leu Leu His Ala Pro Ala
245 250 255

Thr Val Cys Gly Pro Lys Lys Ser Thr Asn Leu Val Lys Asn Lys Cys
260 265 270

Val Asn Phe His His His His His His
275 280

<210> SEQ ID NO 48
<211> LENGTH: 282
<212> TYPE: PRT
<213> ORGANISM: Artificial Sequence
<220> FEATURE:
<223> OTHER INFORMATION: amino acid sequence of the fusion protein
Sp-GvTag002-RBD-His

<400> SEQUENCE: 48

Met Gly Ile Leu Pro Ser Pro Gly Met Pro Ala Leu Leu Ser Leu Val
1 5 10 15

Ser Leu Leu Ser Val Leu Leu Met Gly Cys Val Ala Gly Ser Gly Lys
20 25 30

Lys Val Gly Asn Thr Ile Val Met Val Asp Lys Leu Lys Glu Val Pro
35 40 45

Thr Pro Gly Ser Gly Arg Val Gln Pro Thr Glu Ser Ile Val Arg Phe
50 55 60

Pro Asn Ile Thr Asn Leu Cys Pro Phe Gly Glu Val Phe Asn Ala Thr
65 70 75 80

Arg Phe Ala Ser Val Tyr Ala Trp Asn Arg Lys Arg Ile Ser Asn Cys
85 90 95

Val Ala Asp Tyr Ser Val Leu Tyr Asn Ser Ala Ser Phe Ser Thr Phe
100 105 110

Lys Cys Tyr Gly Val Ser Pro Thr Lys Leu Asn Asp Leu Cys Phe Thr
115 120 125

Asn Val Tyr Ala Asp Ser Phe Val Ile Arg Gly Asp Glu Val Arg Gln
130 135 140

Ile Ala Pro Gly Gln Thr Gly Lys Ile Ala Asp Tyr Asn Tyr Lys Leu
145 150 155 160

Pro Asp Asp Phe Thr Gly Cys Val Ile Ala Trp Asn Ser Asn Asn Leu
165 170 175

Asp Ser Lys Val Gly Gly Asn Tyr Asn Tyr Leu Tyr Arg Leu Phe Arg
180 185 190

Lys Ser Asn Leu Lys Pro Phe Glu Arg Asp Ile Ser Thr Glu Ile Tyr
195 200 205

Gln Ala Gly Ser Thr Pro Cys Asn Gly Val Glu Gly Phe Asn Cys Tyr
210 215 220

Phe Pro Leu Gln Ser Tyr Gly Phe Gln Pro Thr Asn Gly Val Gly Tyr
225 230 235 240

Gln Pro Tyr Arg Val Val Val Leu Ser Phe Glu Leu Leu His Ala Pro
245 250 255

Ala Thr Val Cys Gly Pro Lys Lys Ser Thr Asn Leu Val Lys Asn Lys
260 265 270

Cys Val Asn Phe His His His His His His
275 280

<210> SEQ ID NO 49
<211> LENGTH: 281
<212> TYPE: PRT
<213> ORGANISM: Artificial Sequence
<220> FEATURE:
<223> OTHER INFORMATION: amino acid sequence of the fusion protein
Sp-GvTagOpti-RBD-His

<400> SEQUENCE: 49

Met Gly Ile Leu Pro Ser Pro Gly Met Pro Ala Leu Leu Ser Leu Val
1 5 10 15

-continued

```
Ser Leu Leu Ser Val Leu Leu Met Gly Cys Val Ala Gly Ser Gly Lys
            20                  25                  30

Val Gly Asn Thr Ile Val Met Val Asp Lys Leu Lys Glu Val Pro Thr
        35                  40                  45

Pro Gly Ser Gly Arg Val Gln Pro Thr Glu Ser Ile Val Arg Phe Pro
    50                  55                  60

Asn Ile Thr Asn Leu Cys Pro Phe Gly Glu Val Phe Asn Ala Thr Arg
65                  70                  75                  80

Phe Ala Ser Val Tyr Ala Trp Asn Arg Lys Arg Ile Ser Asn Cys Val
                85                  90                  95

Ala Asp Tyr Ser Val Leu Tyr Asn Ser Ala Ser Phe Ser Thr Phe Lys
            100                 105                 110

Cys Tyr Gly Val Ser Pro Thr Lys Leu Asn Asp Leu Cys Phe Thr Asn
        115                 120                 125

Val Tyr Ala Asp Ser Phe Val Ile Arg Gly Asp Glu Val Arg Gln Ile
    130                 135                 140

Ala Pro Gly Gln Thr Gly Lys Ile Ala Asp Tyr Asn Tyr Lys Leu Pro
145                 150                 155                 160

Asp Asp Phe Thr Gly Cys Val Ile Ala Trp Asn Ser Asn Asn Leu Asp
                165                 170                 175

Ser Lys Val Gly Gly Asn Tyr Asn Tyr Leu Tyr Arg Leu Phe Arg Lys
            180                 185                 190

Ser Asn Leu Lys Pro Phe Glu Arg Asp Ile Ser Thr Glu Ile Tyr Gln
        195                 200                 205

Ala Gly Ser Thr Pro Cys Asn Gly Val Glu Gly Phe Asn Cys Tyr Phe
    210                 215                 220

Pro Leu Gln Ser Tyr Gly Phe Gln Pro Thr Asn Gly Val Gly Tyr Gln
225                 230                 235                 240

Pro Tyr Arg Val Val Val Leu Ser Phe Glu Leu Leu His Ala Pro Ala
                245                 250                 255

Thr Val Cys Gly Pro Lys Lys Ser Thr Asn Leu Val Lys Asn Lys Cys
            260                 265                 270

Val Asn Phe His His His His His His
        275                 280
```

COMBINATION OF PEPTIDE LINKERS FOR PROTEIN COVALENT SELF-ASSEMBLY USING SPONTANEOUS ISOPEPTIDE BOND

CROSS-REFERENCE TO RELATED APPLICATION

This application is a 371 of international application of PCT application serial no. PCT/CN2022/083430, filed on Mar. 28, 2022, which claims the priority benefit of China application no. 202110444350.7 and 202110876301.0, filed on Apr. 23, 2021 and Jul. 31, 2021, respectively. The entirety of each of the above-mentioned patent applications is hereby incorporated by reference herein and made a part of this specification.

1. TECHNICAL FIELD

The present disclosure relates the technical field of protein self-assembly, in particular to, a combination of peptide linkers for protein covalent self-assembly using a spontaneous isopeptide bond.

2. BACKGROUND ART

Cell function depends upon the interaction of a large number of non-covalent proteins-proteins; and the precise arrangement of proteins in a complex influences and determines their functions. Non-covalent interaction is always relatively weak, and even will be usually interrupted under the conditions such as, long period or some mechanical force. Therefore, the ability to design the interaction of covalent proteins-proteins can bring a series of new opportunities for Basic Research, Synthetic Biology, and Biotechnology.

The interaction of covalent proteins is usually mediated by a disulfide bond; but disulfide bond is reversible and not suitable for the reduction of cellular space, and even may disturb protein folding. Due to small molecular weight, peptide tag minimizes its interference on protein functions and thus, it is a common tool to analyze and modify a protein. Gene coding is conducted very easily via a peptide tag; due to its small size, biosynthesis costs and immunogenic interference introduced will be reduced. However, there is a little of higher affinity in the interaction between a peptide tag and a protein, which thus limits its effect in the formation of a stable complex.

Currently, the protein capable of spontaneously forming an isopeptide bond has been always applied to develop a peptide tag, and is covalently bound to the corresponding binding polypeptide thereof (i.e., a linker of the two parts) mutually, thus providing irreversible interaction. The protein capable of spontaneously forming an isopeptide bond can be expressed as two fragments: a peptide tag and a polypeptide binding partner. These two fragments can achieve covalent recombination via the formation of an isopeptide bond, such that molecules or components connected to the peptide tag and the polypeptide binding partner, respectively are fused.

Isopeptide bond is an amido bond formed between side-chain carboxyl groups or side-chain amino groups. In the case of typical biological conditions, such a bond is chemically nonreversible and is resistant to most of proteases. Isopeptide bond is covalent chemically and thus able to produce ultra-strong protein binding effects. On the condition that noncovalent interaction will be dissociated rapidly, e.g., high temperature, high pressure, rigorous chemical treatment or long period, the isopeptide bond formed between a peptide tag and its polypeptide binding partner can still achieve stable binding.

There exist some proteins having very strong interaction in some Gram-positive bacteria. For example, the fibronectin-binding protein (FbaB) of *Streptococcus pyogenes* applied to the fields of therapeutics, biological materials and vaccines contains an adhesin domain (CnaB2); the 31st lysine (K) and the 117th aspartic acid (D) in the domain can spontaneously form an isopeptide bond under the catalysis of the 77th glutamic acid (E). In the previous scientific researches, the CnaB2 of *Streptococcus pyogenes* FbaB protein have been divided into a SpyTag peptide having 13 residues and a SpyCatcher peptide having 116 residues to establish a Spy Tag/SpyCatcher system, thus achieving gene coding and covalent interaction between peptides and proteins. The SpyTag/SpyCatcher system provides a simple, specific and genetic-coding method to create various biological materials, for use in multiple aspects, including biological materials, next generation sequencing (NGS), enzyme stabilization, vaccine development, etc.

Even though the SpyTag/SpyCatcher technology has been applied to multiple aspects, the reaction speed and efficiency are still lower. To improve such a situation, on the one hand, an existing SpyTag/SpyCatcher sequence, e.g., a SpyTag003/SpyCatcher003 system is modified and optimized. On the other hand, a protein capable of spontaneously forming an isopeptide bond in other bacteria can be sought, so as to establish a more excellent linking system.

SUMMARY OF THE INVENTION

The objective of the present disclosure is to overcome the above shortcomings in the prior art, and to provide a combination of peptide linkers for protein covalent self-assembly using a spontaneous isopeptide bond.

The first objective of the present disclosure is to provide a combination of peptide linkers for protein covalent self-assembly using a spontaneous isopeptide bond.

A second objective of the present disclosure is to provide a recombinant and synthetic peptide chain.

A third objective of the present disclosure is to provide a nucleic acid molecule.

A fourth objective of the present disclosure is to provide a vector.

A fifth objective of the present disclosure is to provide a cell.

A sixth objective of the present disclosure is to provide use of any of the combination in self-assembling two molecules or components using an isopeptide bond.

A seventh objective of the present disclosure is to provide a method for self-assembling two molecules or components using an isopeptide bond.

An eighth objective of the present disclosure is to provide a kit for self-assembling two molecules or components using an isopeptide bond.

A ninth objective of the present disclosure is to provide use of one or more of the combination, the nucleic acid molecule, the vector, or the cell in preparing a kit for self-assembling two molecules or components, or in self-assembling two molecules or components using an isopeptide bond.

To achieve the above objectives, the present disclosure is achieved through the following technical solution:

In the present disclosure, GvTag/SdCatcher (SEQ ID NO: 11 and SEQ ID NO: 5), PsTag/SdCatcher (SEQ ID NO: 13 and SEQ ID NO: 5), and SaTag/SdCatcher (SEQ ID NO: 14 and SEQ ID NO: 5) are applied to establish a combined polypeptide-peptide tag linking system capable of spontaneously forming an isopeptide bond. Further, corresponding amino acids are modified and optimized at the N terminal of the peptide tag GvTag such that the binding efficiency is stronger than that of the SpyTag003/SpyCatcher003 system.

Specifically, the other 10 bacteria having a CnaB2 adhesin domain sequence are found via alignment with the CnaB2 sequence of *Streptococcus pyogenes*. These bacteria may include *Gardnerella vaginalis* (Gv), *Granulicatella balaenopterae* (Gb), *Peptostreptococcus* sp (Ps), *Streptococcus anginosus* subsp (Sa), *Streptococcus dysgalactiae* (Sd), *Anaerobutyricum hallii* (Ah), *Clostridium perfringens* (Cp), *Ruminococcus* sp (Rs), *Streptococcus constellatus* (Sco), and *Streptococcus pneumoniae* (Spn).

In the present disclosure, to obtain an isopeptide bond system with higher binding efficiency, the corresponding CnaB2 is decomposed into a Tag peptide and a Catcher protein, to establish 10 different Tag-GFP clones and 10 different Catcher-HPF clones, and then these clones are expressed and purified in an *E. coli* system. Based on the yield of the expression proteins, Catcher proteins of *Peptostreptococcus* sp, *Streptococcus anginosus* subsp, and *Streptococcus dysgalactiae* (PsCatcher, SaCatcher, and SdCatcher) are picked out and incubated with the Tag-GFP of the 10 bacteria above in a way of permutation and combination. Protein electrophoresis and Coomassie brilliant blue are applied to screen out three combinations with more efficient binding capacity, e.g., the combination of SdCatcher and GvTag-GFP, the combination of SdCatcher and PsTag-GFP, and the combination of SdCatcher and SaTag-GFP.

These three forms of combinations are then applied to a Receptor Binding Domain (RBD) subunit nanovaccine system of the S protein of SARS-CoV-2 novel coronavirus. Results show that GvTag-RBD and SdCatcher-HP are self-assembled to a spherical tetracosemer nanoparticle. The use of GvTag/SdCatcher, PsTag/SdCatcher, and SaTag/SdCatcher has effectively improved binding efficiency compared to the existing Spy Tag/SpyCatcher system. Moreover, the protein binding efficiency is optimal when using the GvTag/SdCatcher system. The GvTag sequence is further optimized to obtain a GvTagOpti/SdCatcher system which may further improve the binding efficiency.

Mice are immunized with the RBD-ferritin subunit tetracosemer antigen nanoparticle obtained from the linking systems GvTagOpti/SdCatcher, PsTag/SdCatcher, and SaTag/SdCatcher, which may overcome the shortcoming of insufficient immunogenicity of the RBD monomer, effectively trigger stronger immunoreaction, and improve antibody titer. The linking systems GvTagOpti/SdCatcher, PsTag/SdCatcher, and SaTag/SdCatcher of the present disclosure can significantly improve the reaction efficiency of molecules or components fused to a peptide tag and polypeptide thereof, and has a simple preparation method and a high protein expression level.

Therefore, the present disclosure sets forth the following features:

A combination of peptide linkers for protein covalent self-assembly using a spontaneous isopeptide bond, including a peptide linker 1 (a polypeptide) and a peptide linker 2 (a peptide tag); the peptide linker 1 contains a peptide chain having an amino acid sequence as shown in SEQ ID NO: 5, and the peptide linker 2 contains any one or more of peptide chains having amino acid sequences as shown in SEQ ID NO: 11, SEQ ID NO: 13, and SEQ ID NO: 14.

```
SEQ ID NO: 5:
SGETGQSGNTTIEEDSTTHVKFSKRDINGKELAGAMIELRNLSGQTIQS
WVSDGTVKDFYLMPGTYQFVETAAPEGYELAAPITFTIDEKGQIWVDST
LIVGDDPI;

SEQ ID NO: 11:
NTIVMVDKLKEVPTP;

SEQ ID NO: 13:
NTIVMVDKLKKTP;

SEQ ID NO: 14:
NTIVMVDKLKELPPP.
```

Preferably, the peptide linker 2 contains a peptide chain having an amino acid sequence as shown in SEQ ID NO: 11.

More preferably, the peptide linker 2 contains a peptide chain having an amino acid sequence as shown in SEQ ID NO: 46 (the peptide chain as shown in SEQ ID NO: 11 further has three KVG amino acids at the N terminal).

```
SEQ ID NO: 46:
KVGNTIVMVDKLKEVPTP.
```

The present disclosure further sets forth a recombinant and synthetic peptide chain, including one or more of the peptide linker 1 and/or the peptide linker 2 in the combination according to any one of claim 1 or claim 2.

The present disclosure further sets forth a nucleic acid molecule, including one or more nucleotide sequences encoding the peptide linker 1 and/or the peptide linker 2 in any one of the combinations.

The present disclosure further sets forth a vector, including the nucleic acid molecule.

The present disclosure further sets forth a cell, including the nucleic acid molecule or the vector.

The present disclosure further sets forth use of any of the combination in self-assembling two molecules or components using an isopeptide bond; the two molecules or components are connected with the peptide linker 1 (polypeptide) and the peptide linker 2 (peptide tag) in the combination, respectively.

Further, the present disclosure sets forth a method for self-assembling two molecules or components using an isopeptide bond, including:

- providing a first molecule or a first component containing the peptide linker 1 in the combination according to claim 1 or claim 2;
- providing a second molecule or a second component containing the peptide linker 2 in the combination according to claim 1 or claim 2; and
- contacting the first molecule or the first component with the second molecule or the second component in the case of spontaneously forming an isopeptide bond between the peptide linker 1 and the peptide linker 2, such that the first molecule or the first component is self-assembled with the second molecule or the second component to form a complex using the isopeptide bond.

Furthermore, the present disclosure sets forth a kit for self-assembling two molecules or components using an isopeptide bond, including: one of the peptide linker 1 (polypeptide) and the peptide linker 2 (peptide tag) in the combination, the nucleic acid molecule encoding the peptide linker 1 and the peptide linker 2 in the combination, and a cell containing a vector encoding the peptide linker 1 and the peptide linker 2 in the combination.

The present disclosure further sets forth use of one or more of the combination, the nucleic acid molecule, the vector, and the cell in preparing a kit for self-assembling two molecules or components, or in self-assembling two molecules or components using an isopeptide bond, falling within the protection scope of the present disclosure.

Compared with the prior art, the present disclosure has the following beneficial effects:

The present disclosure constructs novel protein self-assembly systems GvTag/SdCatcher, PsTag/SdCatcher, and SaTag/SdCatcher based on an isopeptide bond, which effectively solves the problem of low binding efficiency of an existing SpyTag/SpyCatcher system, can significantly improve the reaction efficiency of molecules or components fused to a peptide tag and polypeptide thereof, and has a binding efficiency stronger than that of a Spy Tag003/SpyCatcher003 system. Moreover, the GvTagOpti/SdCatcher system, the PsTag/SdCatcher system, and the SaTag/SdCatcher system of the present disclosure have a simple preparation method and a high protein expression level.

DETAILED DESCRIPTION OF THE EMBODIMENTS

The present disclosure is described in detail below with reference to the accompanying drawings and specific examples. The examples are merely used to explain the present disclosure, but not construed as limiting the scope of the present disclosure. The test methods used in the following examples are conventional methods unless otherwise specified; the materials and reagents used are commercially available reagents and materials unless otherwise specified.

Example 1 Obtaining of Bacteria Having a Sequence of a CnaB2 Adhesin Domain

I. Experimental Method

Bacteria having a sequence of a CnaB2 adhesin domain were found via alignment with the CnaB2 sequence of *Streptococcus pyogenes.*

II. Experimental Results

Figure 1:
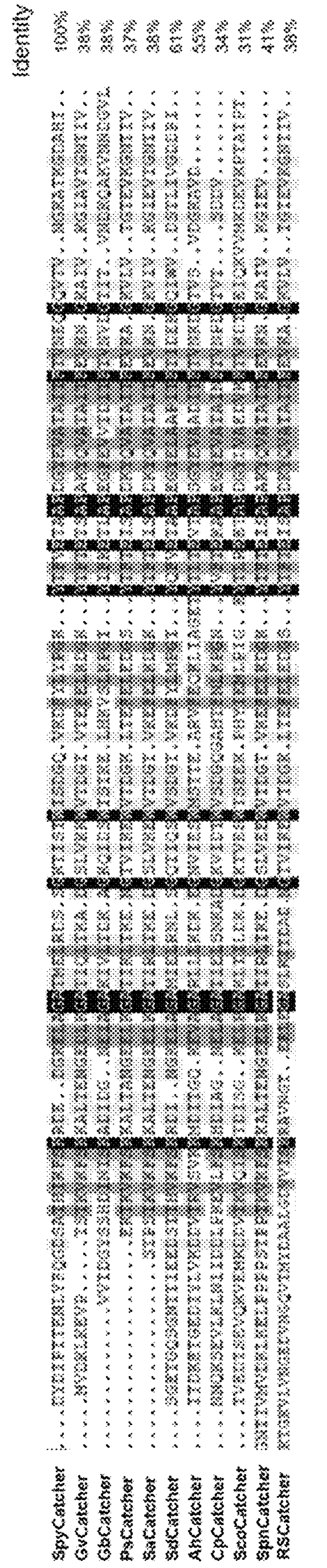
FIG. 1 shows sequence alignment of Catcher polypeptides from different bacteria with SpyCatcher.
Figure 2:
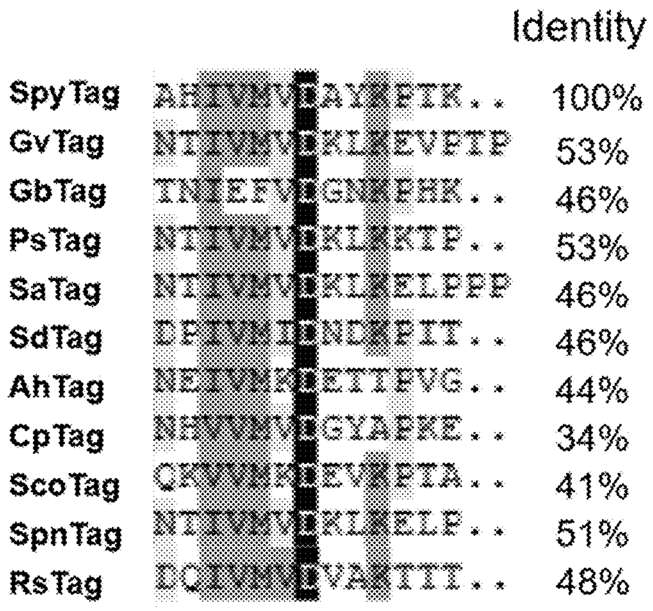
FIG. 2 shows sequence alignment of Tag peptides from different bacteria with Spy Tag.

The sequence alignment of the Catcher polypeptides from different bacteria with SpyCatcher, the sequence alignment of the Tag peptide with Spytag, as well as structure diagrams of the fusion proteins Tag-GFP and Catcher-HPF are shown in FIGS. 1-2, respectively. The other 10 bacteria having a sequence of a CnaB2 adhesin domain were found via alignment with the CnaB2 sequence of *Streptococcus pyogenes*. These bacteria may include *Gardnerella vaginalis* (Gv), *Granulicatella balaenopterae* (Gb), *Peptostreptococcus* sp (Ps), *Streptococcus anginosus* subsp (Sa), *Streptococcus dysgalactiae* (Sd), *Anaerobutyricum hallii* (Ah), *Clostridium perfringens* (Cp), *Ruminococcus* sp (Rs), *Streptococcus constellatus* (Sco), and *Streptococcus pneumoniae* (Spn).

Example 2 Construction of Novel Catcher-HPF and Tag-GFP Fusion Proteins, Screening of a Combination with High Protein-Binding Efficiency

I. Experimental Method

1. Separation of the Sequence of a CnaB2 Adhesin Domain

10 Catcher polypeptide sequences (amino acid sequences are shown in SEQ ID NOs: 1-10, respectively) and 10 Tag peptides (amino acid sequences are shown in SEQ ID NOs: 11-20, respectively) from 10 bacteria, e.g., Gv, Gb, Ps, Sa, Sd, Ah, Cp, Rs, Sco, and Spn.

```
(amino acid sequence of GvCatcher)
                                        SEQ ID NO: 1
MVDKLKEVPTSTKVKFSKKALTENGEDLKGATIQLTKADGSLVKKWVTD
GTVTEFELKDGKYTFTETSAPAKYQVATAITFEVKNGKAIVKGIAVTGN
TIV;

(amino acid sequence of GbCatcher)
                                        SEQ ID NO: 2
VVTDGYSSHDINISKADIDGNEIAGAKIVLTDKAGKQIDSWTSTKELHK
VSLKPGTYIFKETLAPEGFEVVTDITFTVNVDGTITVNDKQAKVNNDGV
L;
```

-continued (amino acid sequence of PsCatcher)
SEQ ID NO: 3
EKTKVKFSKKALTANGEELKGATIKLTKENGTVIKEWVTDGKLTEFELE
DGSYTFTEISAPDKYQVATAITFEVKAGKVLVTGTEVKGNTIV;

(amino acid sequence of SaCatcher)
SEQ ID NO: 4
STPSTKVKFSKKALTENGEELKGATIRLTKEDGSLVKEWVTDGTVKEFE
LKDGKYTFTEISAPDKYQVATAITFEVKNGKVIVKGIEVTGNTIV;

(amino acid sequence of SdCatcher);
SEQ ID NO: 5
SGETGQSGNTTIEEDSTTHVKFSKRDINGKELAGAMIELRNLSGQTIQS
WVSDGTVKDFYLMPGTYQFVETAAPEGYELAAPITFTIDEKGQIWVDST
LIVGDDPI;

(amino acid sequence of AhCatcher)
SEQ ID NO: 6
ITDKETGEDIYLVKDDVTRVSVKKMDITGQKEVAGARLLLKDKEGNVIE
SWMSTTEARVFEQKLIAGETYTLTEVTAPSGYEVAADITFTVNKDGTVS
VDGKAVD;

(amino acid sequence of CpCatcher)
SEQ ID NO: 7
NNQKSEVLKLNIIDDLPKEVLFSKHDIAGNELAGATIELSNKADGKVID
TWVSDGQGAHTFNLKPGNYVFTEKAAPEGYEVATAINFTVNPDGTVTSD
DV;

(amino acid sequence of RSCatcher);
SEQ ID NO: 8
TFTIDKTGKVLVNGEDVNGQVTMYDAALGDVVISKRAVNGTEELEGASL
KITDADGKTVAEWVSDSTPKTIQLDAGTYTLTEETAPDGYTVAESIEFV
VDAAG;

(amino acid sequence of ScoCatcher);
SEQ ID NO: 9
TVEDTSEVQKVEMKDDVTKVQISKTDISGKELPGAKLTILDKDGKTVES
WTSEEKPHYIEMLPIGEYTLREETAPDGYLVAEDVKFTVKDTGEIQKVV
MKDEVKPTATPT;

(amino acid sequence of SpnCatcher);
SEQ ID NO: 10
GNTIVMVDKLKELPPPPSTPPTKVKFSKKALTENGEELKGATIRLTKED
GSLVEEWVTDGTVKEFELKDGKYTFTEISAPAKYQVATAITFEVKNGKA
IVKGIEV;

-continued

SEQ ID NO: 11 (amino acid sequence of GvTag):
NTIVMVDKLKEVPTP;

SEQ ID NO: 12 (amino acid sequence of GbTag):
TNIEFVDGNKPHK;

SEQ ID NO: 13 (amino acid sequence of PsTag):
NTIVMVDKLKKTP;

SEQ ID NO: 14 (amino acid sequence of SaTag):
NTIVMVDKLKELPPP;

SEQ ID NO: 15 (amino acid sequence of SdTag):
DPIVMIDNDKPIT;

SEQ ID NO: 16 (amino acid sequence of AhTag):
NEIVMKDETTPVG;

SEQ ID NO: 17 (amino acid sequence of CpTag):
NHVVMVDGYAPKE;

SEQ ID NO: 18 (amino acid sequence of RSTag):
DQIVMVDVAKTTT;

SEQ ID NO: 19 (amino acid sequence of ScoTag):
QKVVMKDEVKPTA;
and

SEQ ID NO: 20 (amino acid sequence of SpnTag):
NTIVMVDKLKELP.

2. Construction of a Catcher-HPF Fusion Protein Clone, a Tag-GFP Fusion Protein Clone, and a Recombinant Vector Thereof The above 10 different Catcher proteins and *Helicobacter pylori*_Ferritin (HPF) were used to construct 10 types of Catcher-HPF fusion proteins (amino acid sequences are shown in SEQ ID NOs: 21-30) according to the schematic diagram of FIG. 3; the nucleotide sequence encoding each Catcher-HPF fusion protein was cloned between restriction enzyme cutting sites Nco I and Xho I of an expression vector pET28a, to obtain a recombinant vector. The expression vector pET28a has a 6×His Tag and a termination codon at downstream of the restriction enzyme cutting site Xho I. One of the expression vectors pET28a-SdCatcher-HPF is shown in FIG. 4.

SEQ ID NO: 21 (amino acid sequence of the fusion protein GvCatcher-HPF):
MVDKLKEVPTSTKVKFSKKALTENGEDLKGATIQLTKADGSLVKKWVTDGTV

TEFELKDGKYTFTETSAPAKYQVATAITFEVKNGKAIVKGIAVTGNTIVGSGDIIKLL

NEQVNKEMQSSNLYMSMSSWCYTHSLDGAGLFLFDHAAEEYEHAKKLIIFLNENNV

PVQLTSISAPEHKFEGLTQIFQKAYEHEQHISESINNIVDHAIKSKDHATFNFLQWYV

AEQHEEEVLFKDILDKIELIGNENHGLYLADQYVKGIAKSRKS;

SEQ ID NO: 22 (amino acid sequence of the fusion protein GbCatcher-HPF):
VVTDGYSSHDINISKADIDGNEIAGAKIVLTDKAGKQIDSWTSTKELHKVSLKP

GTYIFKETLAPEGFEVVTDITFTVNVDGTITVNDKQAKVNNDGVLGSGDIIKLLNEQ

VNKEMQSSNLYMSMSSWCYTHSLDGAGLFLFDHAAEEYEHAKKLIIFLNENNVPVQ

LTSISAPEHKFEGLTQIFQKAYEHEQHISESINNIVDHAIKSKDHATFNFLQWYVAEQ

HEEEVLFKDILDKIELIGNENHGLYLADQYVKGIAKSRKS;

SEQ ID NO: 23 (amino acid sequence of the fusion protein PsCatcher-HPF):
EKTKVKFSKKALTANGEELKGATIKLTKENGTVIKEWVTDGKLTEFELEDGSY

TFTEISAPDKYQVATAITFEVKAGKVLVTGTEVKGNTIVGSGDIIKLLNEQVNKEMQ

-continued

SSNLYMSMSSWCYTHSLDGAGLFLFDHAAEEYEHAKKLIIFLNENNVPVQLTSISAP

EHKFEGLTQIFQKAYEHEQHISESINNIVDHAIKSKDHATFNFLQWYVAEQHEEEVLF

KDILDKIELIGNENHGLYLADQYVKGIAKSRKS;

SEQ ID NO: 24 (amino acid sequence of the fusion protein SaCatcher-HPF):
STPSTKVKFSKKALTENGEELKGATIRLTKEDGSLVKEWVTDGTVKEFELKDG

KYTFTEISAPDKYQVATAITFEVKNGKVIVKGIEVTGNTIVGSGDIIKLLNEQVNKEM

QSSNLYMSMSSWCYTHSLDGAGLFLFDHAAEEYEHAKKLIIFLNENNVPVQLTSISA

PEHKFEGLTQIFQKAYEHEQHISESINNIVDHAIKSKDHATFNFLQWYVAEQHEEEVL

FKDILDKIELIGNENHGLYLADQYVKGIAKSRKS;

SEQ ID NO: 25 (amino acid sequence of the fusion protein SdCatcher-HPF):
SGETGQSGNTTIEEDSTTHVKFSKRDINGKELAGAMIELRNLSGQTIQSWVSDG

TVKDFYLMPGTYQFVETAAPEGYELAAPITFTIDEKGQIWVDSTLIVGDDPIGSGDIIK

LLNEQVNKEMQSSNLYMSMSSWCYTHSLDGAGLFLFDHAAEEYEHAKKLIIFLNEN

NVPVQLTSISAPEHKFEGLTQIFQKAYEHEQHISESINNIVDHAIKSKDHATFNFLQW

YVAEQHEEEVLFKDILDKIELIGNENHGLYLADQYVKGIAKSRKS;

SEQ ID NO: 26 (amino acid sequence of the fusion protein AhCatcher-HPF):
ITDKETGEDIYLVKDDVTRVSVKKMDITGQKEVAGARLLLKDKEGNVIESWM

STTEARVFEQKLIAGETYTLTEVTAPSGYEVAADITFTVNKDGTVSVDGKAVDGSGD

IIKLLNEQVNKEMQSSNLYMSMSSWCYTHSLDGAGLFLFDHAAEEYEHAKKLIIFLN

ENNVPVQLTSISAPEHKFEGLTQIFQKAYEHEQHISESINNIVDHAIKSKDHATFNFLQ

WYVAEQHEEEVLFKDILDKIELIGNENHGLYLADQYVKGIAKSRKS;

SEQ ID NO: 27 (amino acid sequence of the fusion protein CpCatcher-HPF):
NNQKSEVLKLNIIDDLPKEVLFSKHDIAGNELAGATIELSNKADGKVIDTWVSD

GQGAHTFNLKPGNYVFTEKAAPEGYEVATAINFTVNPDGTVTSDDVGSGDIIKLLNE

QVNKEMQSSNLYMSMSSWCYTHSLDGAGLFLFDHAAEEYEHAKKLIIFLNENNVPV

QLTSISAPEHKFEGLTQIFQKAYEHEQHISESINNIVDHAIKSKDHATFNFLQWYVAE

QHEEEVLFKDILDKIELIGNENHGLYLADQYVKGIAKSRKS;

SEQ ID NO: 28 (amino acid sequence of the fusion protein RSCatcher-HPF):
TFTIDKTGKVLVNGEDVNGQVTMYDAALGDVVISKRAVNGTEELEGASLKIT

DADGKTVAEWVSDSTPKTIQLDAGTYTLTEETAPDGYTVAESIEFVVDAAGGSGDII

KLLNEQVNKEMQSSNLYMSMSSWCYTHSLDGAGLFLFDHAAEEYEHAKKLIIFLNE

NNVPVQLTSISAPEHKFEGLTQIFQKAYEHEQHISESINNIVDHAIKSKDHATFNFLQ

WYVAEQHEEEVLFKDILDKIELIGNENHGLYLADQYVKGIAKSRKS;

SEQ ID NO: 29 (amino acid sequence of the fusion protein ScoCatcher-HPF):
TVEDTSEVQKVEMKDDVTKVQISKTDISGKELPGAKLTILDKDGKTVESWTSE

EKPHYIEMLPIGEYTLREETAPDGYLVAEDVKFTVKDTGEIQKVVMKDEVKPTATPT

GSGDIIKLLNEQVNKEMQSSNLYMSMSSWCYTHSLDGAGLFLFDHAAEEYEHAKKL

IIFLNENNVPVQLTSISAPEHKFEGLTQIFQKAYEHEQHISESINNIVDHAIKSKDHATF

NFLQWYVAEQHEEEVLFKDILDKIELIGNENHGLYLADQYVKGIAKSRKS;

SEQ ID NO: 30 (amino acid sequence of the fusion protein SpnCatcher-HPF):
GNTIVMVDKLKELPPPPSTPPTKVKFSKKALTENGEELKGATIRLTKEDGSLVE

EWVTDGTVKEFELKDGKYTFTEISAPAKYQVATAITFEVKNGKAIVKGIEVGSGDIIK

LLNEQVNKEMQSSNLYMSMSSWCYTHSLDGAGLFLFDHAAEEYEHAKKLIIFLNEN

-continued

NVPVQLTSISAPEHKFEGLTQIFQKAYEHEQHISESINNIVDHAIKSKDHATFNFLQW

YVAEQHEEEVLFKDILDKIELIGNENHGLYLADQYVKGIAKSRKS.

Figure 3:
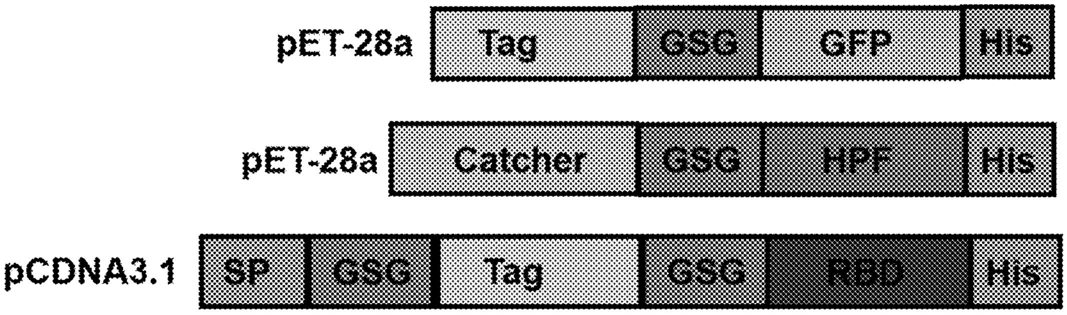
FIG. 3 is a schematic diagram showing structures of fusion proteins Tag-GFP, Catcher-HPF, and Tag-RBD.
Figure 4:
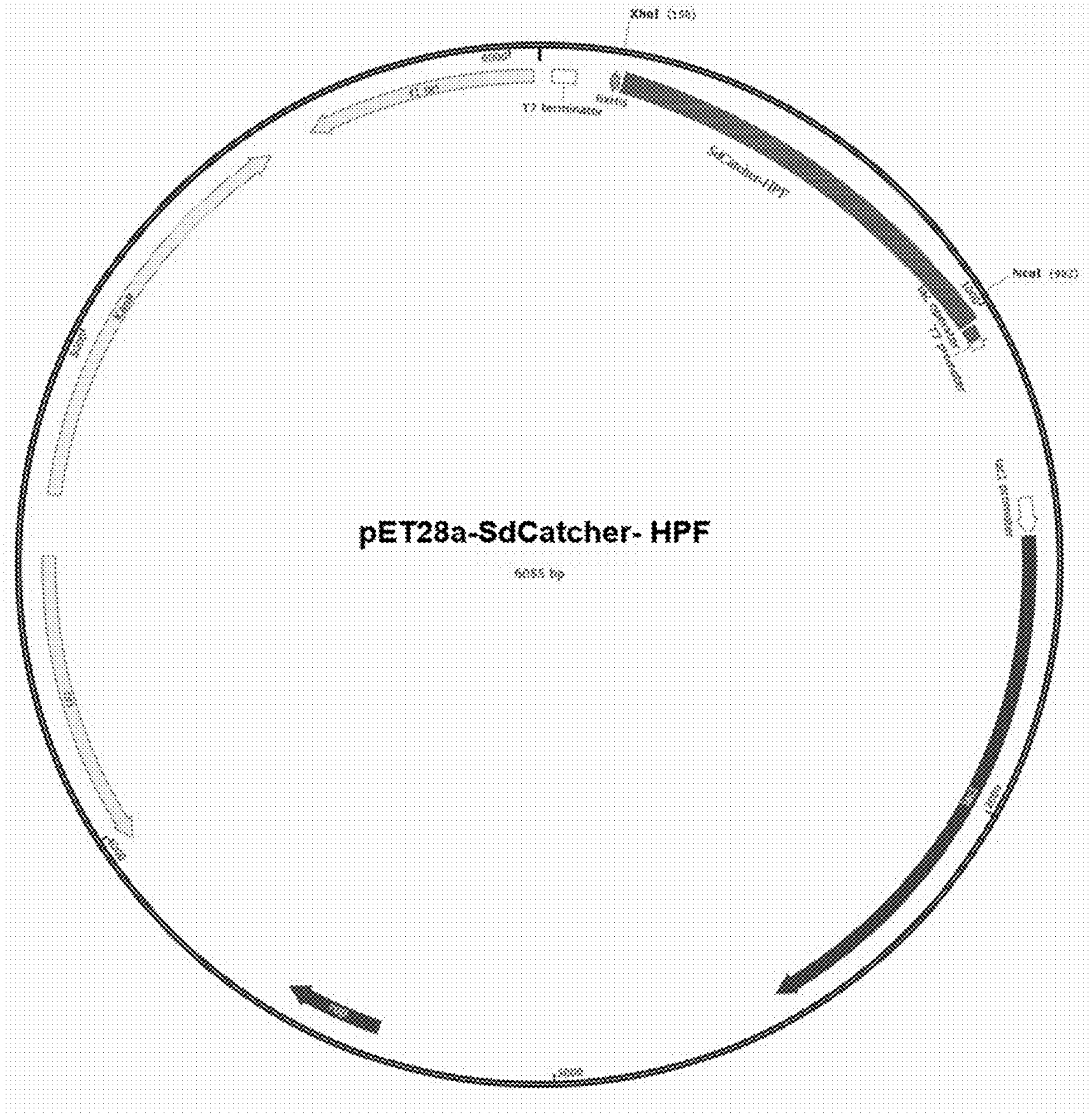
FIG. 4 is a structure diagram of a plasmid expressing SdCatcher-HPF.
Figure 5:
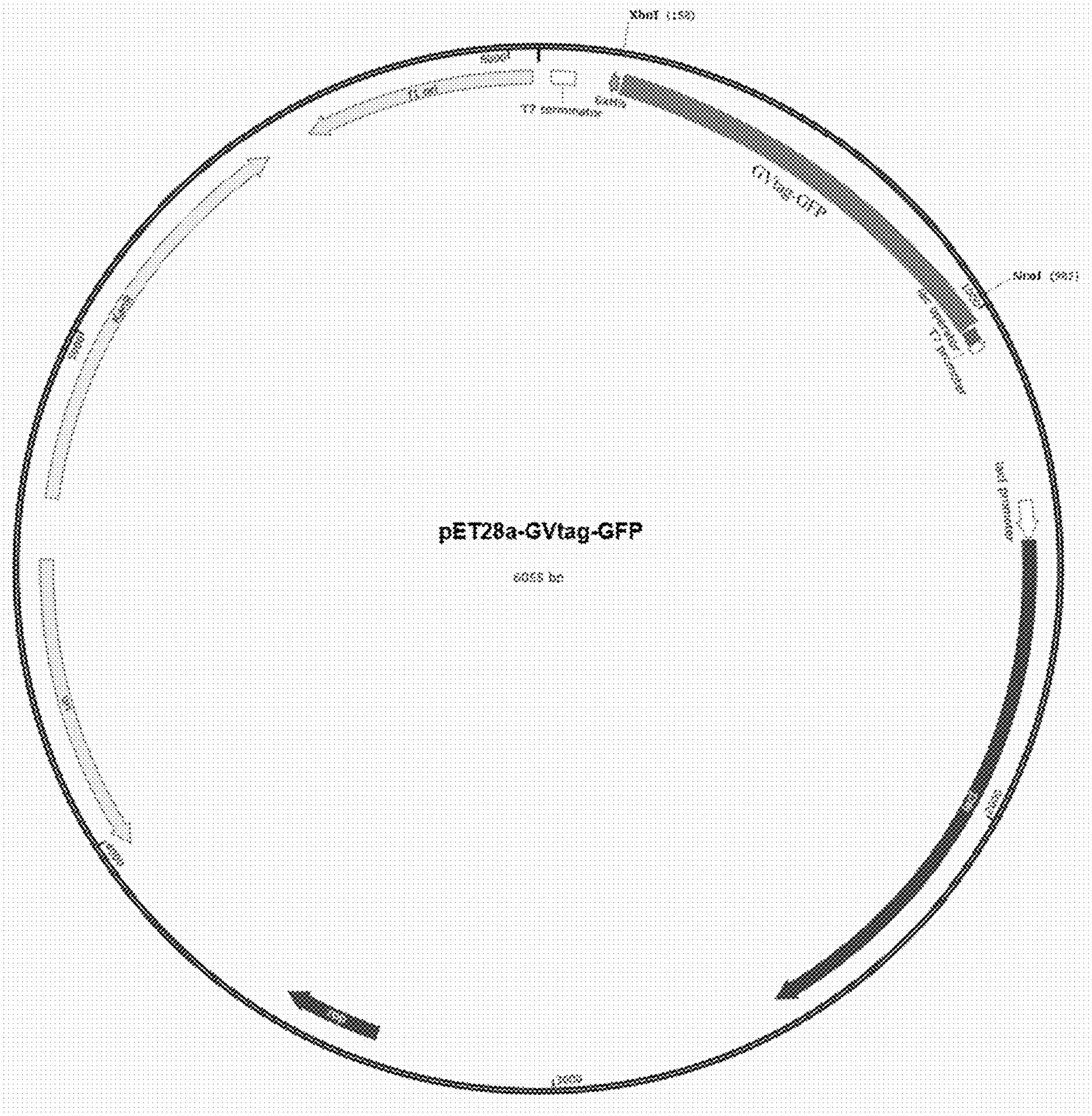
FIG. 5 is a structure diagram of a plasmid expressing GvTag-GFP.

The 10 different Tag proteins and green fluorescent protein (GFP) were used to construct 10 types of Tag-GFP fusion protein clones (amino acid sequences are shown in SEQ ID NOs: 31-40) according to the schematic diagram of FIG. 3; the nucleotide sequence encoding each Tag-GFP fusion protein was cloned between restriction enzyme cutting sites Nco I and Xho I of an expression vector pET28a, to obtain a recombinant plasmid. One of the expression vectors pET28a-GvTag-GFP is shown in FIG. 5.

SEQ ID NO: 31 (amino acid sequence of the fusion protein GvTag-GFP):
NTIVMVDKLKEVPTPGSGMVSKGEELFTGVVPILVELDGDVNGHKFSVSGEGE

GDATYGKLTLKFICTTGKLPVPWPTLVTTLTYGVQCFSRYPDHMKQHDFFKSAMPE

GYVQERTIFFKDDGNYKTRAEVKFEGDTLVNRIELKGIDFKEDGNILGHKLEYNYNS

HNVYIMADKQKNGIKVNFKIRHNIEDGSVQLADHYQQNTPIGDGPVLLPDNHYLST

QSALSKDPNEKRDHMVLLEFVTAAGITLGMDELYK;

SEQ ID NO: 32 (amino acid sequence of the fusion protein GbTag-GFP):
TNIEFVDGNKPHKGSGMVSKGEELFTGVVPILVELDGDVNGHKFSVSGEGEGD

ATYGKLTLKFICTTGKLPVPWPTLVTTLTYGVQCFSRYPDHMKQHDFFKSAMPEGY

VQERTIFFKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNHYLSTQSA

LSKDPNEKRDHMVLLEFVTAAGITLGMDELYK;

SEQ ID NO: 33 (amino acid sequence of the fusion protein PsTag-GFP):
NTIVMVDKLKKTPGSGMVSKGEELFTGVVPILVELDGDVNGHKFSVSGEGEG

DATYGKLTLKFICTTGKLPVPWPTLVTTLTYGVQCFSRYPDHMKQHDFFKSAMPEG

YVQERTIFFKDDGNYKTRAEVKFEGDTLVNRIELKGIDFKEDGNILGHKLEYNYNSH

NVYIMADKQKNGIKVNFKIRHNIEDGSVQLADHYQQNTPIGDGPVLLPDNHYLSTQS

ALSKDPNEKRDHMVLLEFVTAAGITLGMDELYK;

SEQ ID NO: 34 (amino acid sequence of the fusion protein SaTag-GFP):
NTIVMVDKLKELPPPGSGMVSKGEELFTGVVPILVELDGDVNGHKFSVSGEGE

GDATYGKLTLKFICTTGKLPVPWPTLVTTLTYGVQCFSRYPDHMKQHDFFKSAMPE

GYVQERTIFFKDDGNYKTRAEVKFEGDTLVNRIELKGIDFKEDGNILGHKLEYNYNS

HNVYIMADKQKNGIKVNFKIRHNIEDGSVQLADHYQQNTPIGDGPVLLPDNHYLST

QSALSKDPNEKRDHMVLLEFVTAAGITLGMDELYK;

SEQ ID NO: 35 (amino acid sequence of the fusion protein SdTag-GFP):
DPIVMIDNDKPITGSGMVSKGEELFTGVVPILVELDGDVNGHKFSVSGEGEGD

ATYGKLTLKFICTTGKLPVPWPTLVTTLTYGVQCFSRYPDHMKQHDFFKSAMPEGY

VQERTIFFKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNHYLSTQSA

LSKDPNEKRDHMVLLEFVTAAGITLGMDELYK.

SEQ ID NO: 36 (amino acid sequence of the fusion protein AhTag-GFP):
NEIVMKDETTPVGGSGMVSKGEELFTGVVPILVELDGDVNGHKFSVSGEGEGDATY

GKLTLKFICTTGKLPVPWPTLVTTLTYGVQCFSRYPDHMKQHDFFKSAMPEGYVQE

-continued

RTIFFKDDGNYKTRAEVKFEGDTLVNRIELKGIDFKEDGNILGHKLEYNYNSHNVYI

MADKQKNGIKVNFKIRHNIEDGSVQLADHYQQNTPIGDGPVLLPDNHYLSTQSALS

KDPNEKRDHMVLLEFVTAAGITLGMDELYK;

SEQ ID NO: 37 (amino acid sequence of the fusion protein CpTag-GFP):
NHVVMVDGYAPKEGSGMVSKGEELFTGVVPILVELDGDVNGHKFSVSGEGEGDAT

YGKLTLKFICTTGKLPVPWPTLVTTLTYGVQCFSRYPDHMKQHDFFKSAMPEGYVQ

ERTIFFKDDGNYKTRAEVKFEGDTLVNRIELKGIDFKEDGNILGHKLEYNYNSHNVY

IMADKQKNGIKVNFKIRHNIEDGSVQLADHYQQNTPIGDGPVLLPDNHYLSTQSALS

KDPNEKRDHMVLLEFVTAAGITLGMDELYK;

SEQ ID NO: 38 (amino acid sequence of the fusion protein RSTag-GFP):
DQIVMVDVAKTTTGSGMVSKGEELFTGVVPILVELDGDVNGHKFSVSGEGEGDATY

GKLTLKFICTTGKLPVPWPTLVTTLTYGVQCFSRYPDHMKQHDFFKSAMPEGYVQE

RTIFFKDDGNYKTRAEVKFEGDTLVNRIELKGIDFKEDGNILGHKLEYNYNSHNVYI

MADKQKNGIKVNFKIRHNIEDGSVQLADHYQQNTPIGDGPVLLPDNHYLSTQSALS

KDPNEKRDHMVLLEFVTAAGITLGMDELYK;

SEQ ID NO: 39 (amino acid sequence of the fusion protein ScoTag-GFP):
QKVVMKDEVKPTAGSGMVSKGEELFTGVVPILVELDGDVNGHKFSVSGEGEGDAT

YGKLTLKFICTTGKLPVPWPTLVTTLTYGVQCFSRYPDHMKQHDFFKSAMPEGYVQ

ERTIFFKDDGNYKTRAEVKFEGDTLVNRIELKGIDFKEDGNILGHKLEYNYNSHNVY

IMADKQKNGIKVNFKIRHNIEDGSVQLADHYQQNTPIGDGPVLLPDNHYLSTQSALS

KDPNEKRDHMVLLEFVTAAGITLGMDELYK;

SEQ ID NO: 40 (amino acid sequence of the fusion protein SpnTag-GFP):
NTIVMVDKLKELPGSGMVSKGEELFTGVVPILVELDGDVNGHKFSVSGEGEGDATY

GKLTLKFICTTGKLPVPWPTLVTTLTYGVQCFSRYPDHMKQHDFFKSAMPEGYVQE

RTIFFKDDGNYKTRAEVKFEGDTLVNRIELKGIDFKEDGNILGHKLEYNYNSHNVYI

MADKQKNGIKVNFKIRHNIEDGSVQLADHYQQNTPIGDGPVLLPDNHYLSTQSALS

KDPNEKRDHMVLLEFVTAAGITLGMDELYK.

The specific sequence information is specifically shown in Table 1.

TABLE 1

| | Amino acid sequence of Catcher protein | Amino acid sequence of Tag peptide | Amino acid sequence of the fusion protein Catcher-HPF | Amino acid sequence of the fusion protein Tag-GFP |
|---|---|---|---|---|
| *Gardnerella vaginalis* (Gv) | SEQ ID NO: 1 | SEQ ID NO: 11 | SEQ ID NO: 21 | SEQ ID NO: 31 |
| *Granulicatella balaenopterae* (Gb) | SEQ ID NO: 2 | SEQ ID NO: 12 | SEQ ID NO: 22 | SEQ ID NO: 32 |
| *Peptostreptococcus* sp (Ps) | SEQ ID NO: 3 | SEQ ID NO: 13 | SEQ ID NO: 23 | SEQ ID NO: 33 |
| *Streptococcus anginosus* subsp (Sa) | SEQ ID NO: 4 | SEQ ID NO: 14 | SEQ ID NO: 24 | SEQ ID NO: 34 |
| *Streptococcus dysgalactiae* (Sd) | SEQ ID NO: 5 | SEQ ID NO: 15 | SEQ ID NO: 25 | SEQ ID NO: 35 |
| *Anaerobutyricum hallii* (Ah) | SEQ ID NO: 6 | SEQ ID NO: 16 | SEQ ID NO: 26 | SEQ ID NO: 36 |
| *Clostridium perfringens* (Cp) | SEQ ID NO: 7 | SEQ ID NO: 17 | SEQ ID NO: 27 | SEQ ID NO: 37 |
| *Ruminococcus* sp (Rs) | SEQ ID NO: 8 | SEQ ID NO: 18 | SEQ ID NO: 28 | SEQ ID NO: 38 |

TABLE 1-continued

| | Amino acid sequence of Catcher protein | Amino acid sequence of Tag peptide | Amino acid sequence of the fusion protein Catcher-HPF | Amino acid sequence of the fusion protein Tag-GFP |
|---|---|---|---|---|
| *Streptococcus constellatus* (Sco) | SEQ ID NO: 9 | SEQ ID NO: 19 | SEQ ID NO: 29 | SEQ ID NO: 39 |
| *Streptococcus pneumoniae* (Spn) | SEQ ID NO: 10 | SEQ ID NO: 20 | SEQ ID NO: 30 | SEQ ID NO: 40 |

3. Expression of the Fusion Protein Catcher-HPF and the Fusion Protein Tag-GFP

The prepared 20 recombinant plasmids were transformed into DH5a competent cells, and cultured overnight at 37 °C; positive clones were screened out and PCR-identified. The positive clones were sent for sequencing, and the plasmids was extracted after the sequencing result was correct.

The plasmids with correct sequencing of the 20 recombinant plasmids were transfected into BL21(DE3) to obtain recombinant strains, respectively for the expression of a prokaryotic protein; the recombinant strains were subjected to enlarged culture with kanamycin-resistant LB media at 37 °C and 220 rpm/min until $OD_{600}$ was about 0.6 (about 4 h), and then IPTG with a final concentration of 1 mM was added to induce protein expression at 16 °C and 220 rpm/min. 18 h later after the induction, bacterial cells were dissolved and disrupted ultrasonically; then the solution was centrifuged and precipitate was discarded.

Supernatant was incubated with Ni-NTA agarose (GE Healthcare) to enrich His-labeled Catcher-HPF and Tag-GFP, and then the proteins were eluted by a Tris buffer solution containing imidazole. The purified proteins were concentrated and replaced by 20 mM Tri-HCl+50 mM NaCl buffer solution (pH=7.5). The proteins were subjected to concentration determination by BCA assay and stained by Coomassie blue, to detect the expression of each protein.

4. Incubation of the Tag-GFP and the Catcher-HPF

Each purified Tag-GFP and each purified Catcher-HPF were incubated, respectively. Incubation of the Tag-GFP and the Catcher-HPF in a 20 mM Tri-HCl+50 mM NaCl Tris buffer solution (pH=7.5) according to a molar ratio of 1:1, i.e., 5 nmol of the Tag-GFP and 5 nmol of the Catcher-HPF were put to 1 ml of the buffer solution and incubated for 1 h at room temperature.

II. Experimental Results

Figure 6:
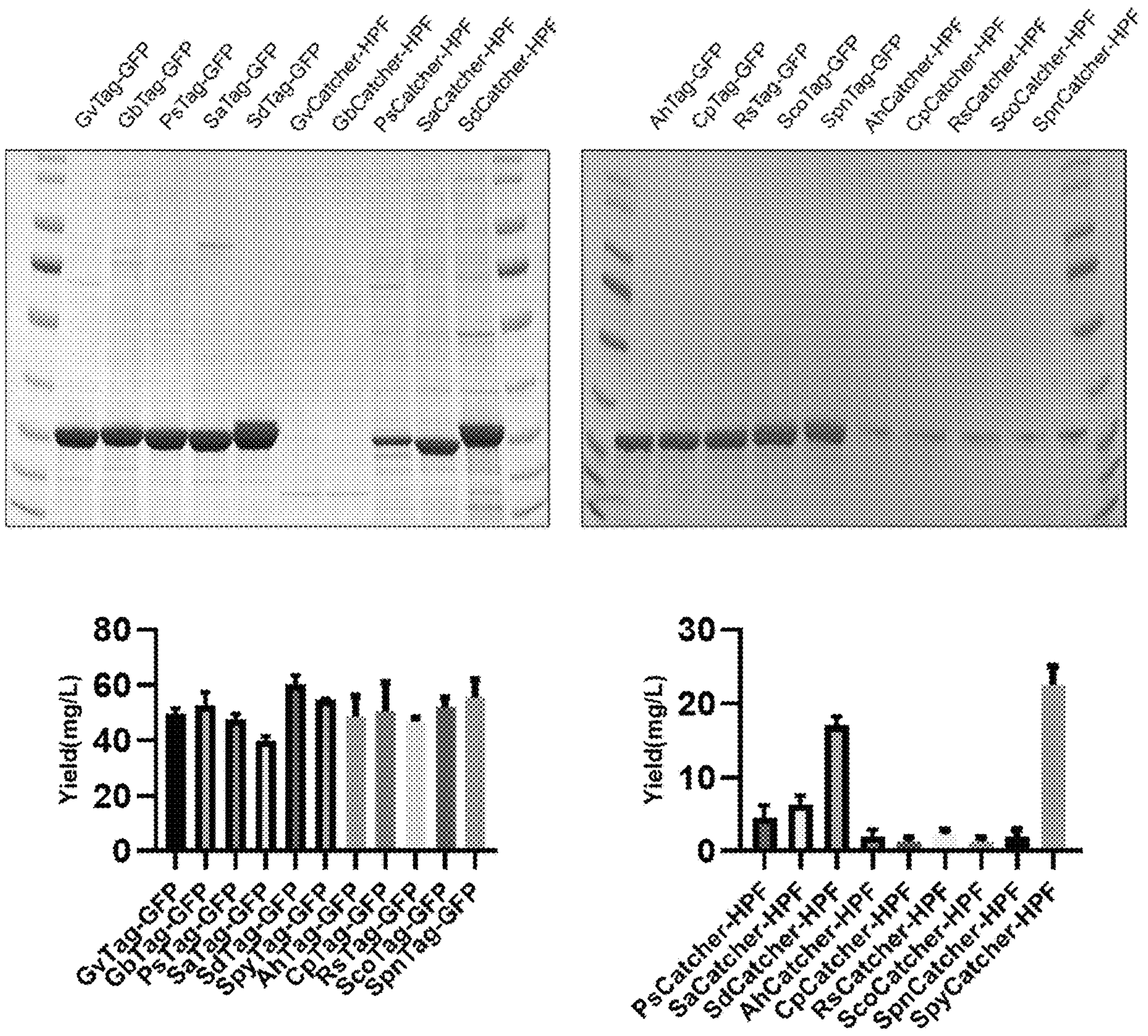
FIG. 6 shows Coomassie Blue staining and protein yield of fusion proteins Tag-GFP and Catcher-HPF from different bacteria.

Coomassie blue staining results are shown in FIG. 6. Ps, Sa and Sd had high expression quantity of Catcher proteins, and these Catcher proteins were incubated with the Tag-GFP from the above five bacteria in a way of permutation and combination.

Figure 7:
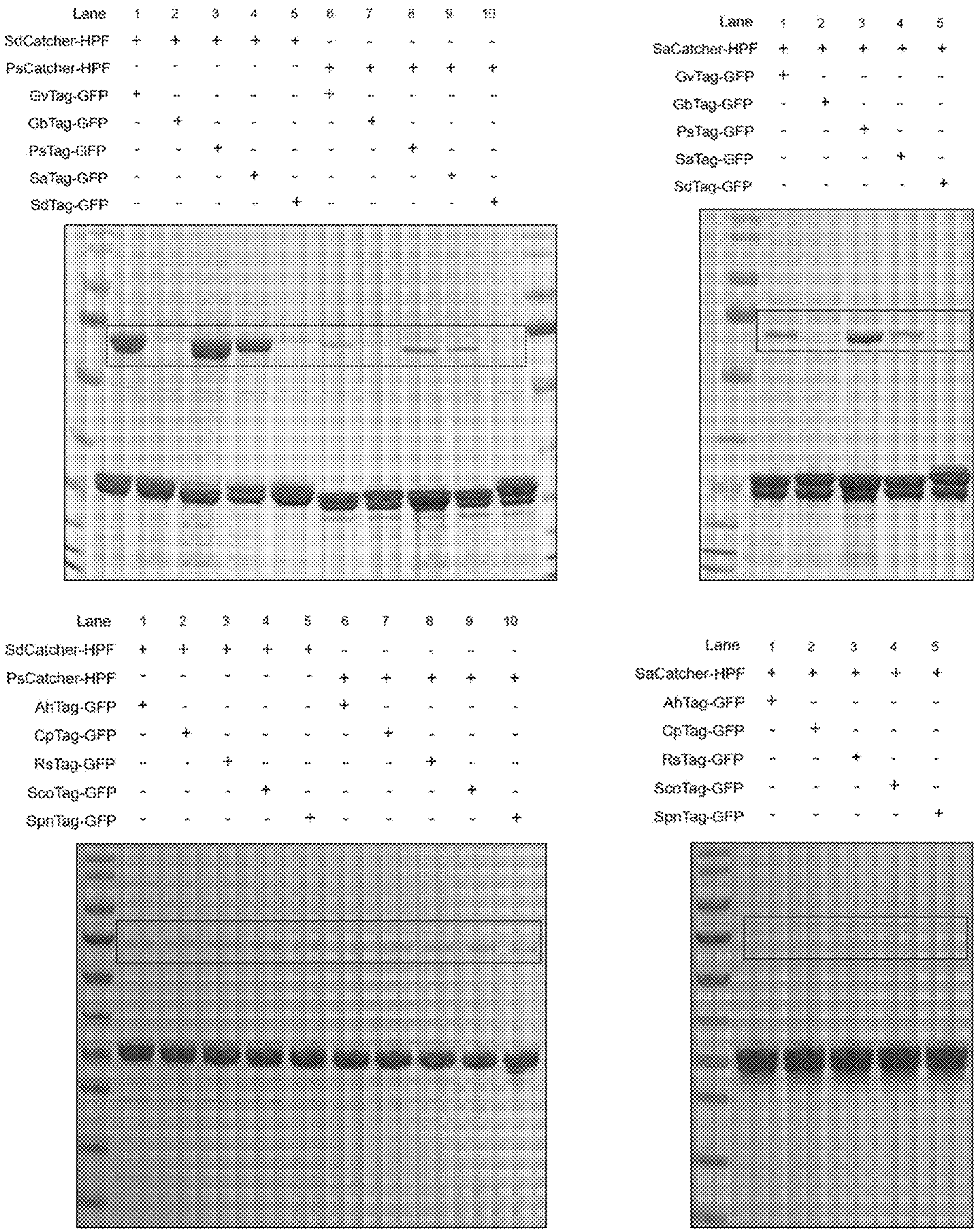
FIG. 7 shows Coomassie Blue staining of binding proteins obtained after the Catcher-HPF proteins from *Peptostreptococcus* sp (Ps), *Streptococcus anginosus* subsp (Sa), and *Streptococcus dysgalactiae* (Sd) are incubated with Tag-GFP from 10 bacteria in a way of permutation and combination.

Incubation results are shown in FIG. 7. After Catcher-HPF and Tag-GFP were bound together, the size of the protein was 65 KDa. The results show the three combinations: the SdCatcher protein of Sd with GvTag-GFP (SEQ ID NO: 31), PsTag-GFP (SEQ ID NO: 33) and SaTag-GFP (SEQ ID NO: 34) have relatively effective binding capacity. Thereby three combined binding systems, namely, GvTag/SdCatcher (SEQ ID NO: 11 and SEQ ID NO: 5), PsTag/SdCatcher (SEQ ID NO: 13 and SEQ ID NO: 5) and SaTag/SdCatcher (SEQ ID NO: 14 and SEQ ID NO: 5) were screened out.

Example 3 Use of these Three Combined Binding Systems to an RBD Subunit Nanovaccine System of the S Protein of Sars-CoV-2 Novel Coronavirus I. Experimental Method These three combined binding systems of GvTag/SdCatcher, PsTag/SdCatcher, and SaTag/SdCatcher screened in Example 2 were then applied to an RBD subunit nanovaccine system of the S protein of SARS-CoV-2 novel coronavirus.

1. Construction of Recombinant Plasmid

Figure 8:
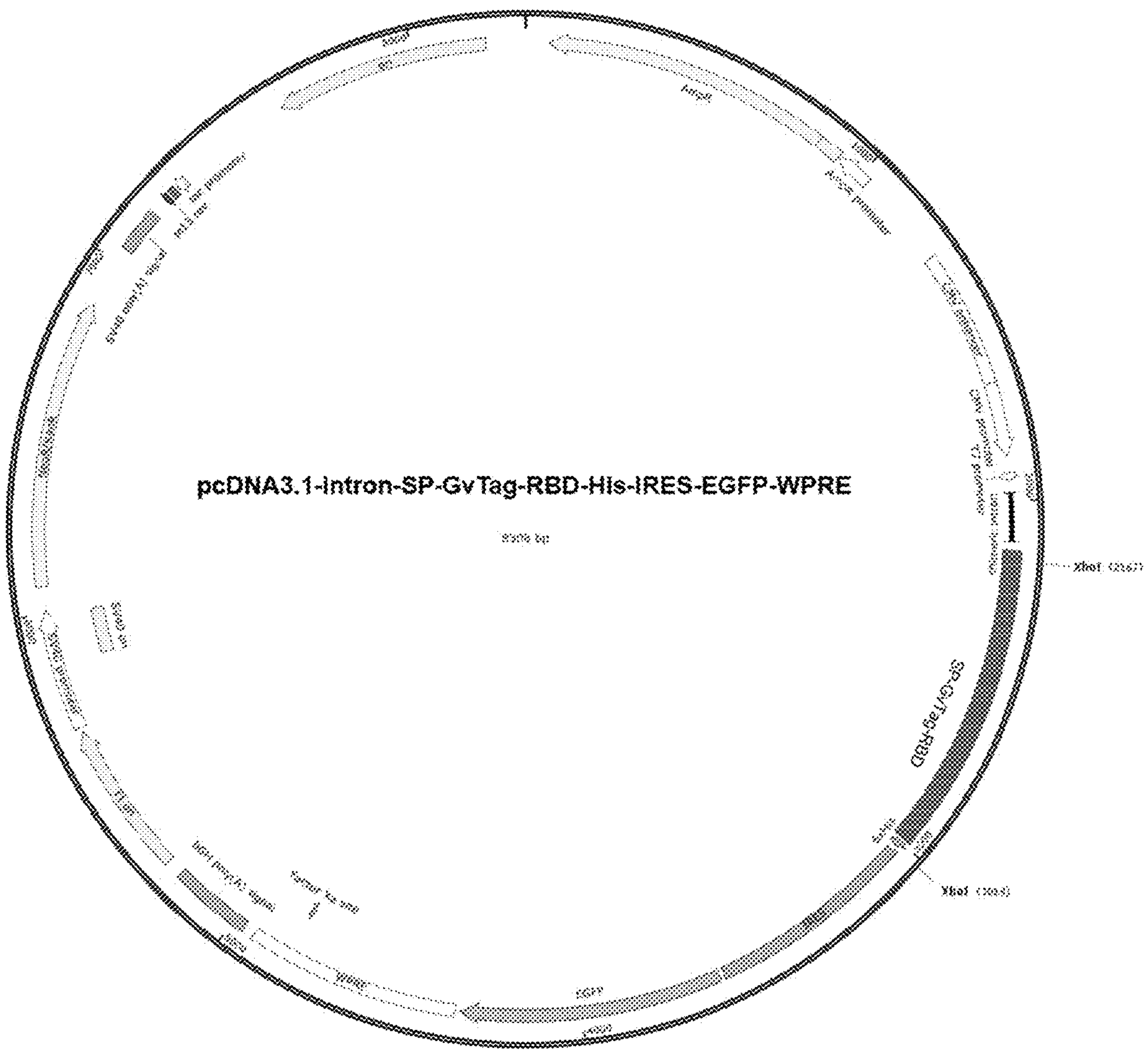
FIG. 8 is a structure diagram showing a plasmid expressing GvTag-RBD.

Three Tag-RBD fusion protein clones were constructed by GvTag, PsTag, and SaTag with RBD, respectively according to the schematic diagram as shown in FIG. 3. A coding sequence for a secreting peptide SP was added at 5' terminal of the Tag-RBD nucleotide sequence; Tag and RBD were spaced by a Linker GSG; 6×His and translation termination codon were added at 3' terminal thereof, so as to obtain SP-GvTag-RBD-His, SP-PsTag-RBD-His and SP-SaTag-RBD-His (amino acid sequences encoded are shown in SEQ ID NOs: 41-43), respectively. SP-GvTag-RBD-His, SP-PsTag-RBD-His and SP-SaTag-RBD-His were then cloned between the restriction enzyme cutting sites Xho I and Xba I of an expression vector (pcDNA3.1-Intron-WPRE) (as shown in FIG. 8) to which Intron and WPRE were added for expression enhancement, thereby constructing an expression vector pcDNA3.1-Intron-SP-Tag-RBD-IRES-GFP-WPRE. One of the expression vectors pcDNA3.1-Intron-SP-GvTag-RBD-His-IRES-GFP-WPRE is shown in FIG. 8.

```
SEQ ID NO: 41 (amino acid sequence of the fusion protein SP-GvTag-RBD-His):
MGILPSPGMP

ALLSLVSLLSVLLMGCVAGSGNTIVMVDKLKEVPTPGSGRVQPTESIVRF

PNITNLCPFG

EVFNATRFASVYAWNRKRISNCVADYSVLYNSASFSTFKCYGVSPTKLND

LCFTNVYADSFVIRGDEVRQIAPGQTGKIADYNYKLPDDFTGCVIAWNSNNLD
```

-continued

```
SKVGGNYNYLYRLFRKSNLKPFERDISTEIYQAGSTPCNGVEGENCYFPLQSYGFQPT

NGVGYQPYRVVVLSFELLH APATVCGPKK STNLVKNKCV NFHHHHHH;

SEQ ID NO: 42 (amino acid sequence of the fusion protein SP-PsTag-RBD-His):
MGILPSPGMPALLSLVSLLSVLLMGCVAGSGNTIVMVDKLKKTPGSGRVQPTE

SIVRFPNITNLCPFGEVFNATRFASVYAWNRKRISNCVADYSVLYNSASFSTFKCYGV

SPTKLNDLCFTNVYADSFVIRGDEVRQIAPGQTGKIADYNYKLPDDFTGCVIAWNSN

NLDSKVGGNYNYLYRLFRKSNLKPFERDISTEIYQAGSTPCNGVEGENCYFPLQSYG

FQPTNGVGYQPYRVVVLSFELLHAPATVCGPKKSTNLVKNKCVNFHHHHHH;

SEQ ID NO: 43 (amino acid sequence of the fusion protein SP-SaTag-RBD-His):
MGILPSPGMPALLSLVSLLSVLLMGCVAGSGNTIVMVDKLKELPPPGSGRVQP

TESIVRFPNITNLCPFGEVFNATRFASVYAWNRKRISNCVADYSVLYNSASFSTFKCY

GVSPTKLNDLCFTNVYADSFVIRGDEVRQIAPGQTGKIADYNYKLPDDFTGCVIAWN

SNNLDSKVGGNYNYLYRLFRKSNLKPFERDISTEIYQAGSTPCNGVEGENCYFPLQS

YGFQPTNGVGYQPYRVVVLSFELLHAPATVCGPKKSTNLVKNKCVNFHHHHHH.
```

2. Expression and Purification of the Recombinant Protein

The prepared recombinant plasmids were transformed into DH5a competent cells, and cultured overnight at 37 °C; positive clones were screened and PCR-identified. Deendotoxin-plasmids were extracted, and transfected into HEK293F cells in a way of lipofection transfection, 5 days alter after the transfection, the cellular supernatant was harvested after centrifuge, and then the interest protein was purified.

The supernatant was incubated with Ni-NTA agarose (GE Healthcare); His-labeled Tag-RBD was enriched and then protein elution was performed by a Tris buffer solution containing imidazole. The purified proteins were concentrated and replaced by 20 mM Tri-HCl+50 mM NaCl buffer solution (pH=7.5). The proteins were subjected to concentration determination by BCA and stained by Coomassie blue.

3. Self-Assembly of Ferritin of a Tetracosemer Nanoparticle 5 nmol of the purified Tag-RBD protein was incubated with 5 nmol of the SdCatcher-HPF protein prokaryotically expressed and purified in Example 3 in 1 ml of buffer system (20 mM Tri-HCl+50 mM NaCl, pH=7.5) for 1 h at room temperature. After the Tag-RBD and the SdCatcher-HPF were bound together, the monomeric protein had a size of 70 KDa.

II. Experimental Results

Figure 9:
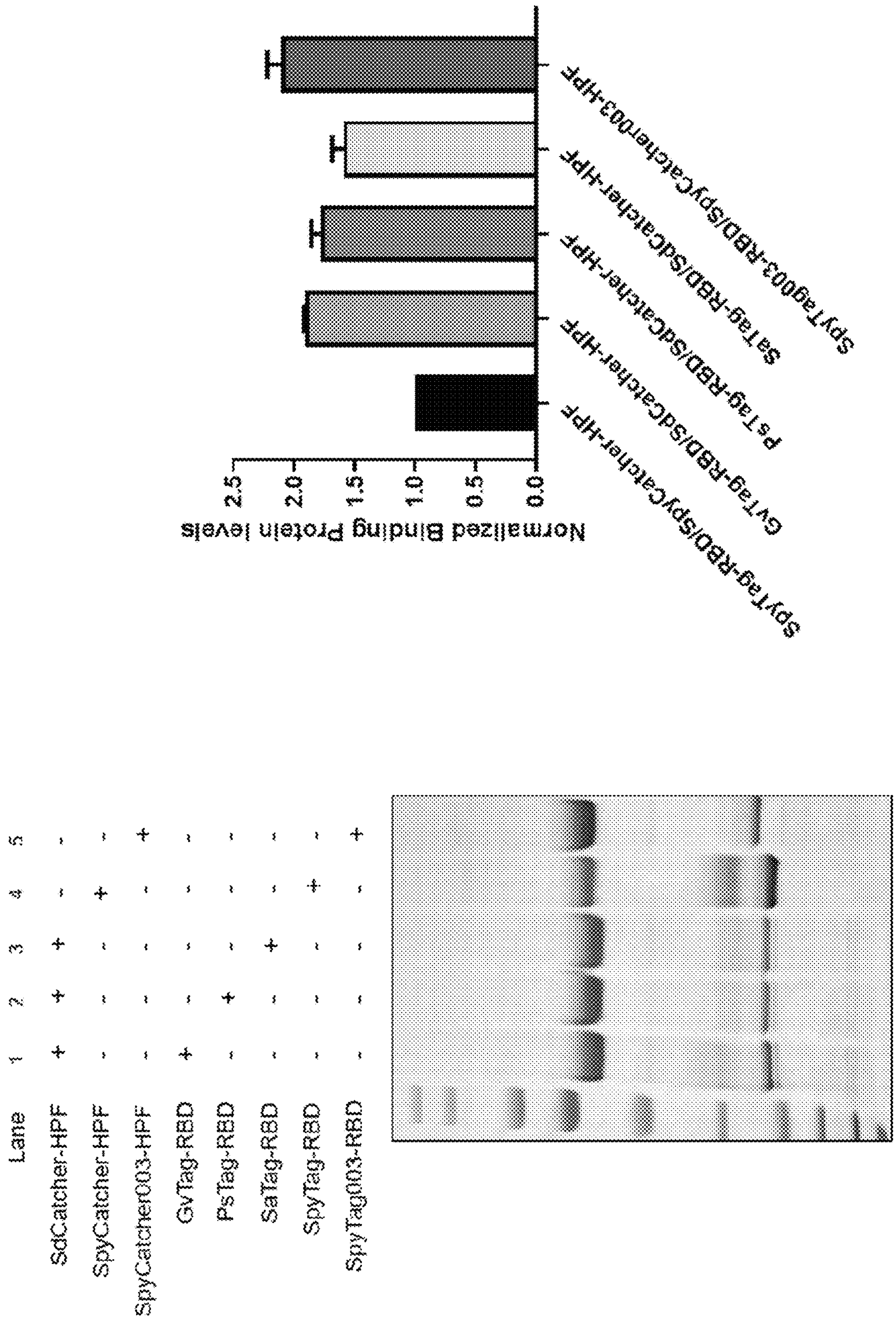
FIG. 9 is a diagram of Coomassie Blue staining showing linking efficiency of binding proteins obtained after three combined linking systems GvTag/SdCatcher, PsTag/SdCatcher and SaTag/SdCatcher, as well as linking systems SpyTag/SpyCatcher and Spy Tag003/SpyCatcher003 are applied to an RBD nanovaccine system of novel coronavirus.

Results are as shown in FIG. 9. The use of GvTag/SdCatcher, PsTag/SdCatcher, and SaTag/SdCatcher has effectively improved binding efficiency compared to the existing SpyTag/SpyCatcher system. Moreover, the protein binding efficiency is optimal when using the GvTag/SdCatcher system, but inferior to the optimized SpyTag003/SpyCatcher003 system.

Example 4 Use of the Optimized GvTag/SdCatcher System to the RBD Subunit Nanovaccine System of the S Protein of Sars-CoV-2 Novel Coronavirus I. Experimental Method Three amino acids RVG were added at N terminal of the GvTag sequence to construct a peptide tag GvTag001 with 18 amino acids (amino acid sequence is shown in SEQ ID NO: 44: RVGNTIVMVDKLKEVPTP); three amino acids KKVG were added at N terminal of the GvTag sequence to construct a peptide tag GvTag002 with 19 amino acids (amino acid sequence is shown in SEQ ID NO: 45: KKVGNTIVMVDKLKEVPTP); three amino acids KVG were added at N terminal of the GvTag sequence to construct a peptide tag GvTagOpti with 18 amino acids (amino acid sequence is shown in SEQ ID NO: 46: KVGNTIVMVDKLKEVPTP); namely, 3 artificially modified GvTags (amino acid sequences are shown in SEQ ID NOs: 44-46, respectively) were obtained.

The 3 artificially modified GvTags (amino acid sequences are shown in SEQ ID NOs: 44-46, respectively) and RBD served to construct fusion protein clones GvTag001-RBD, GvTag002-RBD and GvTagOpti-RBD, respectively according to the schematic diagram as shown in FIG. 3. A coding sequence for a secreting peptide SP was added at each 5' terminal of the nucleotide sequence of GvTag001-RBD, GvTag002-RBD and GvTagOpti-RBD; and a translation termination codon was added at each 3' terminal thereof, so as to obtain SP-GvTag001-RBD-His, SP-GvTag002-RBD-His and SP-GvTagOpti-RBD-His. The amino acid sequences encoded thereby are shown in SEQ ID NOs: 47-49, respectively. SP-GvTag001-RBD-His, SP-GvTag002-RBD-His and SP-GvTagOpti-RBD-His were then cloned between the restriction enzyme cutting sites Xho I and Xba I of an expression vector (pcDNA3.1-Intron-WPRE) to which Intron and WPRE were added for expression enhancement, thereby constructing expression vectors pcDNA3.1-Intron-SP-GvTag001-RBD-His-IRES-GFP-WPR, pcDNA3.1-Intron-SP-GvTag002-RBD-His-IRES-GFP-WPR, and pcDNA3.1-Intron-SP-GvTagOpti-RBD-His-IRES-GFP-WPRE, respectively.

SEQ ID NO: 47 (amino acid sequence of the fusion protein Sp-GvTag001-RBD-His):
MGILPSPGMPALLSLVSLLSVLLMGCVAGSGRVGNTIVMVDKLKEVPTPGSGR

VQPTESIVRFPNITNLCPFGEVFNATRFASVYAWNRKRISNCVADYSVLYNSASFSTF

KCYGVSPTKLNDLCFTNVYADSFVIRGDEVRQIAPGQTGKIADYNYKLPDDFTGCVI

AWNSNNLDSKVGGNYNYLYRLFRKSNLKPFERDISTEIYQAGSTPCNGVEGENCYFP

LQSYGFQPTNGVGYQPYRVVVLSFELLHAPATVCGPKKSTNLVKNKCVNFHHHHH

H;

SEQ ID NO: 48 (amino acid sequence of the fusion protein Sp-GvTag002-RBD-His):
MGILPSPGMPALLSLVSLLSVLLMGCVAGSGKKVGNTIVMVDKLKEVPTPGSG

RVQPTESIVRFPNITNLCPFGEVFNATRFASVYAWNRKRISNCVADYSVLYNSASFST

FKCYGVSPTKLNDLCFTNVYADSFVIRGDEVRQIAPGQTGKIADYNYKLPDDFTGCV

IAWNSNNLDSKVGGNYNYLYRLFRKSNLKPFERDISTEIYQAGSTPCNGVEGENCYF

PLQSYGFQPTNGVGYQPYRVVVLSFELLHAPATVCGPKKSTNLVKNKCVNFHHHHH

H;

SEQ ID NO.: 49 (amino acid sequence of the fusion protein Sp-GvTagOpti-RBD-His):
MGILPSPGMPALLSLVSLLSVLLMGCVAGSGKVGNTIVMVDKLKEVPTPGSGR

VQPTESIVRFPNITNLCPFGEVFNATRFASVYAWNRKRISNCVADYSVLYNSASFSTF

KCYGVSPTKLNDLCFTNVYADSFVIRGDEVRQIAPGQTGKIADYNYKLPDDFTGCVI

AWNSNNLDSKVGGNYNYLYRLFRKSNLKPFERDISTEIYQAGSTPCNGVEGFNCYFP

LQSYGFQPTNGVGYQPYRVVVLSFELLHAPATVCGPKKSTNLVKNKCVNFHHHHH

H.

The GvTag001-RBD, GvTag002-RBD, and GvTagOpti-RBD proteins were purified by the method of Example 3, respectively. 5 nmol of the purified GvTag001-RBD, GvTag002-RBD and GvTagOpti-RBD were incubated with 5 nmol of the SdCatcher-HPF protein prokaryotically expressed in Example 3 in 1 ml of buffer system (20 mM Tri-HCl+50 mM NaCl, pH=7.5) for 1 h at room temperature.

II. Experimental Results

Figure 10:
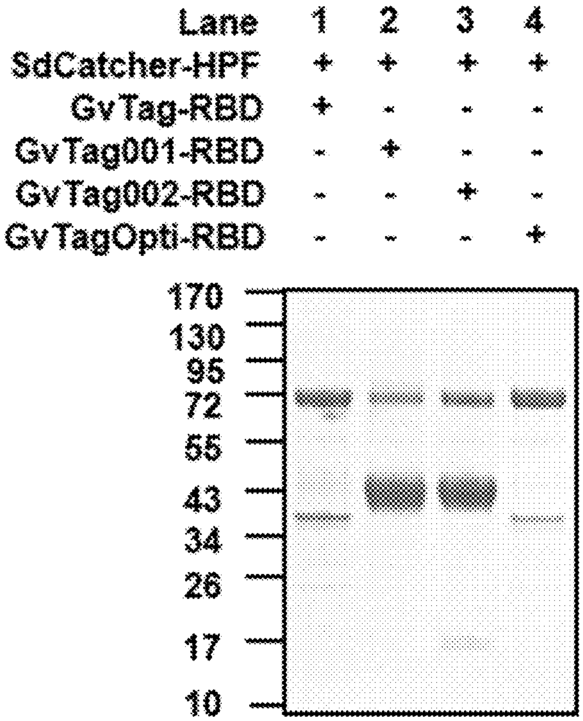
FIG. 10 is a diagram of Coomassie Blue staining showing linking efficiency of binding proteins of the GvTag/SdCatcher, GvTag001/SdCatcher, GvTag002/SdCatcher, and GvTagOpti/SdCatcher systems.

The results are shown in FIG. 10. The amount of the GvTag003-RBD-SdCatcher-HPF polymeric antigen proteins obtained using the GvTagOpti/SdCatcher (SEQ ID NO: 46 and SEQ ID NO: 5) system in this example is more than that of the polymeric antigen proteins obtained using the GvTag/SdCatcher system in Example 3, the GvTag001/SdCatcher (SEQ ID NO: 44 and SEQ ID NO: 5) system in this example, and the GvTag002/SdCatcher (SEQ ID NO: 44 and SEQ ID NO: 5) system in this example.

Example 5 Comparison of the Binding Efficiency Between the GvTagOpti/SdCatcher System and the SpyTag003/SpyCatcher003 System I. Experimental Method 5 nmol of the GvTagOpti-RBD protein obtained in Example 4 was bound to 5 nmol of the SdCatcher-HPF obtained in Example 3, and then diluted by a 20 mM Tri-HCl+50 mM NaCl buffer solution (pH=7.5) at the dilution ratio of 1:2, 1:5 and 1:10. The specific operating steps were as follows: 5 nmol of the GvTagOpti-RBD protein obtained in Example 4 was incubated with 5 nmol of the SdCatcher-HPF obtained in Example 3 in 1 ml of a buffer system (20 mM Tri-HCl+50 mM NaCl) at room temperature for 1 h to obtain a solution A; 50 μl of the solution A was then added to 50 μl of 20 mM Tri-HCl+50 mM NaCl buffer solution (diluted at 1:2) to obtain a solution B. 40 μl of the solution B was added to 60 μl of 20 mM Tri-HCl+50 mM NaCl buffer solution (diluted at 1:5) to obtain a solution C. 50 μl of the solution C was then added to 50 μl of 20 mM Tri-HCl+50 mM NaCl buffer solution (diluted at 1:10) to obtain a solution D. 20 μl of the solution B, 20 μl of the solution C, and 20 μl of the solution D were then pipetted into three 1.5 ml EP tubes, respectively, and 5 μl of 5×loading was added respectively to each tube for protein boiling at 100 °C. After being boiled for 5 min, 20 μl of each sample was subjected to protein electrophoresis and Coomassie brilliant blue staining.

Similarly, 5 nmol of the SpyTag003-RBD protein was bound to 5 nmol of the SdCatcher003-HPF, and then diluted by a 20 mM Tri-HCl+50 mM NaCl buffer solution (pH=7.5) at the dilution ratio of 1:2, 1:5 and 1:10. The specific operating steps are described above. The diluted binding proteins were then compared in sequence.

II. Experimental Results

Figure 11:
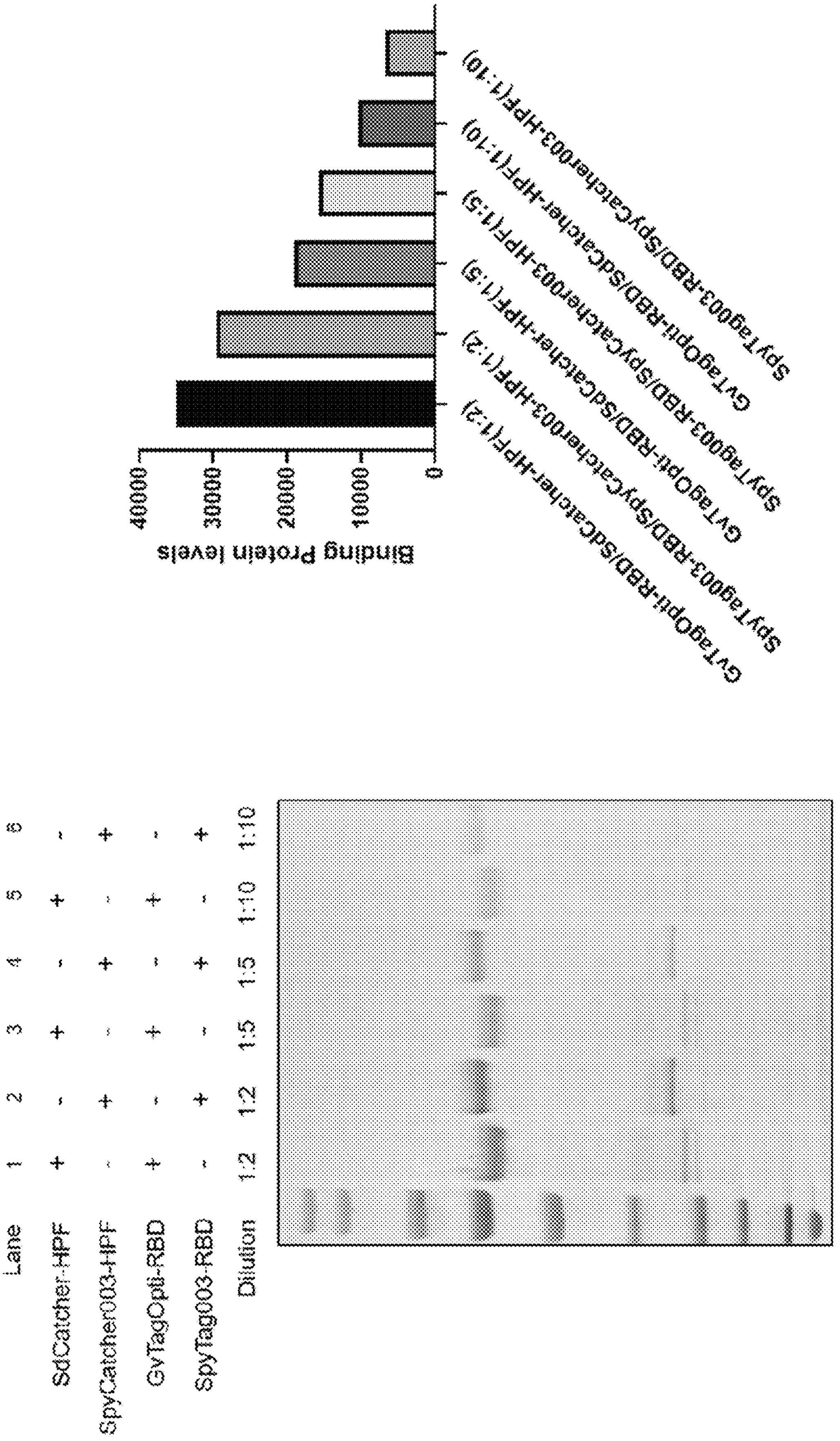
FIG. 11 is a diagram of Coomassie Blue staining showing protein linking efficiency of the GvTagOpti/SdCatcher and Spy Tag003/SpyCatcher003systems.

The results are shown in FIG. 11. In the RBD subunit nanovaccine system of SARS-CoV-2 novel coronavirus, the GvTagOpti/SdCatcher (SEQ ID NO: 46 and SEQ ID NO: 5) in Example 4 has strong binding efficiency than that of the SpyTag003/SpyCatcher003 system.

Example 6

I. Experimental Method

Figure 12:
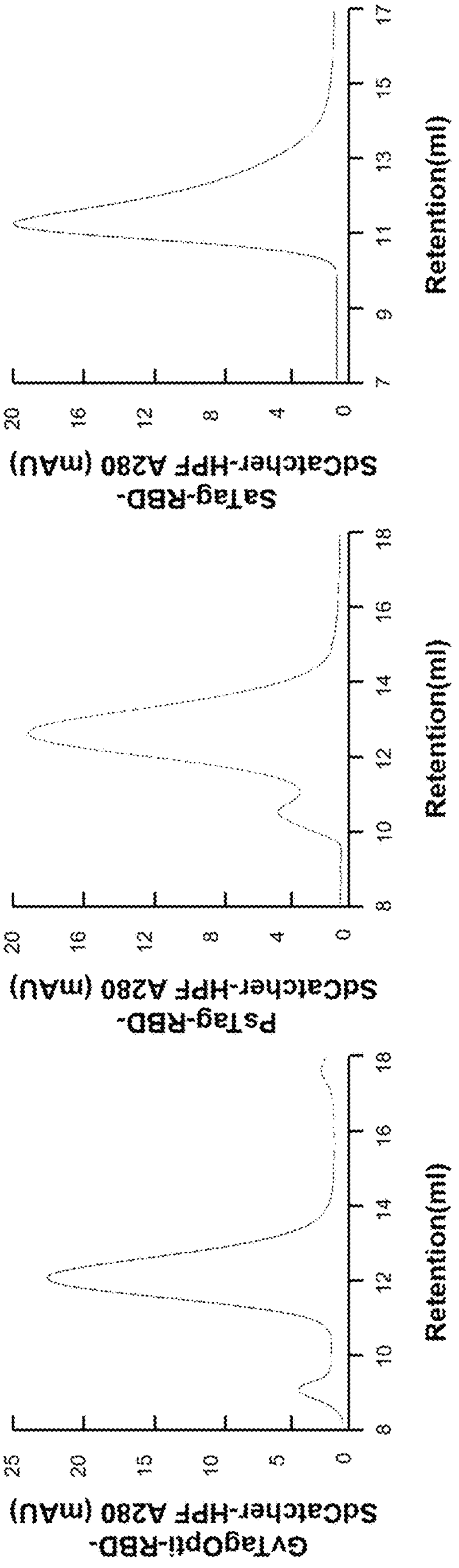
FIG. 12 shows purification of RBD-HPF proteins linked using an isopeptide bond of the GvTagOpti/SdCatcher system, the PsTag/SdCatcher system, and the SaTag/SdCatcher system by molecular sieve.

The purified GvTagOpti-RBD-SdCatcher-HPF polymeric antigen obtained from Example 4, the purified PsTag-RBD- SdCatcher-HPF polymeric antigen and SaTag-RBD-SdCatcher-HPF obtained from Example 3 were purified by molecular sieve chromatography with a Siperose6 Increase10/300 GL column (GE), to obtain the tetracosemer RBD-HPF proteins (as shown in FIG. 12). The buffer solution for molecular sieve chromatography was: 20 mM Tri-HCl+50 mM NaCl, pH=7.5. After being concentrated, the interest proteins were diluted with 20 mM Tri-HCl+50 mM NaCl (pH=7.5) to 100 μl according to Table 2, and then emulsified with an Alum adjuvant with same volume in groups.

TABLE 2

| Antigen/Control | Antigen content | Adjuvant | Quantity of animals (pcs.) |
|---|---|---|---|
| PBS | 0 | Alum | 5 |
| SpyTag003-RBD (monomer) | 0.2 nM | Alum | 5 |
| GvTagOpti-RBD-SdCatcher-HPF (Example 4) | 0.2 nM | Alum | 5 |
| PsTag-RBD-SdCatcher-HPF (Example 3) | 0.2 nM | Alum | 5 |
| SaTag-RBD-SdCatcher-HPF (Example 3) | 0.2 nM | Alum | 5 |
| SpyTag003-RBD-SpyCatcher003-HPF | 0.2 nM | Alum | 5 |

Balb/C mice aged at 6-8 weeks were then grouped and immunized. Each mouse was inoculated in a volume of 200 μl via subcutaneous injection. The mice were subjected to blood sampling from eye sockets on the 14th day. After standing for a period of time, the mice serum was separated out, centrifuged at 4 °C and 2800 rpm for 15 min, and then immediately used for Anti-RBD IgG ELISA test.

II. Experimental Results

Figure 13:
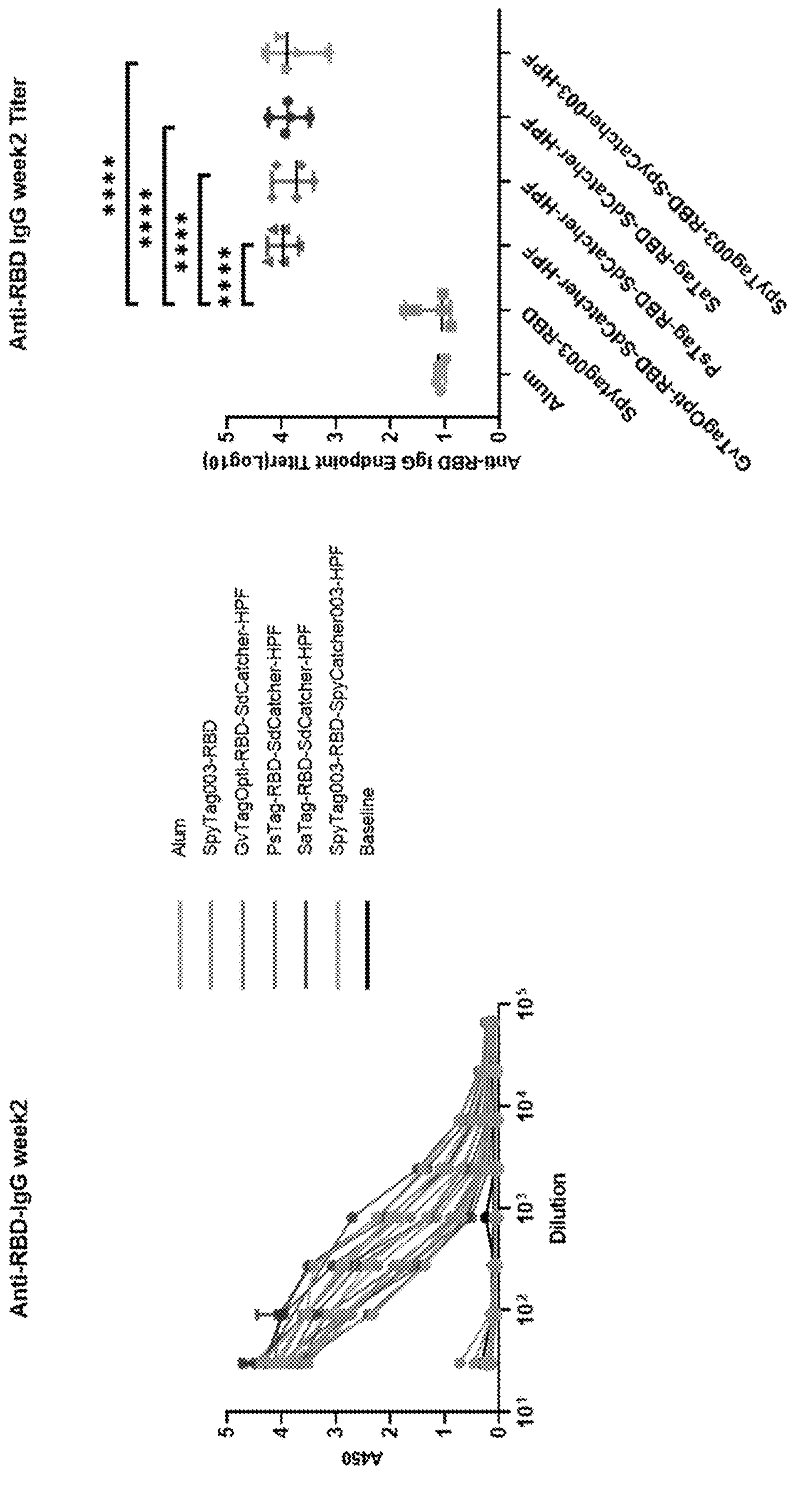
FIG. 13 shows determination of valence of serum RBD antibody after two weeks that mice are immunized with the RBD-HPF proteins linked using an isopeptide bond of the GvTagOpti/SdCatcher system, the PsTag/SdCatcher system, the SaTag/SdCatcher system, and the SpyTag003/SpyCatcher003 system.

The results are shown in FIG. 13. In the GvTagOpti/SdCatcher system (SEQ ID NO: 46 and SEQ ID NO: 5), the PsTag/SdCatcher system (SEQ ID NO: 13 and SEQ ID NO: 5), the SaTag/SdCatcher system (SEQ ID NO: 14 and SEQ ID NO:5), and the SpyTag003/SpyCatcher003 system of the present disclosure, the RBD-HPF proteins linked using an isopeptide bond thereof were emulsified with the Alum adjuvant, respectively, and then immunized mice for once for 14 days, which may stimulate humoral immunity of the mice. Compared with the RBD monomer without the linking system using an isopeptide bond, the RBD-HPF proteins linked using the isopeptide bond of the GvTagOpti/SdCatcher system, the PsTag/SdCatcher system, the SaTag/SdCatcher system, and the SpyTag003/SpyCatcher003 system generated a high titer of Anti-RBD IgG, and had immunogenicity much higher than the RBD monomer.

Finally, it should be indicated that the above examples are merely used to specify the technical solutions of the present disclosure, but not construed as limiting the protection scope of the present disclosure. A person skilled in the art can further make other different forms of alterations or changes on the basis of the above description. Moreover, there is no need and no way to enumerate all the embodiments one by one. Any modification, equivalent substitution and improvement made within the spirit and principle of the present disclosure should fall within the protection scope of the claims of the present disclosure.

What is claimed is:

1. A combination of peptide linkers for protein covalent self-assembly using a spontaneous isopeptide bond, comprising a peptide linker 1 and a peptide linker 2; wherein the peptide linker 1 comprises a peptide chain having an amino acid sequence as shown in SEQ ID NO: 5, and the peptide linker 2 comprises any one or more of peptide chains having amino acid sequences as shown in any one or more of SEQ ID NOs: 11, 13, and 14.

2. The combination of peptide linkers according to claim 1, wherein the peptide linker 2 comprises a peptide chain having an amino acid sequence as shown in SEQ ID NO: 46.

3. A recombinant and synthetic peptide chain, comprising the peptide linker 1 and the peptide linker 2 in the combination of peptide linkers according to claim 1.

4. A nucleic acid molecule, comprising a nucleotide sequence encoding the peptide linker 1 and the peptide linker 2 in the combination of peptide linkers according to claim 1.

5. A vector, comprising the nucleic acid molecule according to claim 4.

6. A cell, comprising the nucleic acid molecule according to claim 4.

7. A method for self-assembling two molecules or components using an isopeptide bond, comprising:

providing a first molecule or a first component comprising the peptide linker 1 in the combination of peptide linkers according to claim 1;

providing a second molecule or a second component comprising the peptide linker 2 in the combination of peptide linkers; and contacting the first molecule or the first component with the second molecule or the second component in a case of spontaneously forming an isopeptide bond between the peptide linker 1 and the peptide linker 2, such that the first molecule or the first component is self-assembled with the second molecule or the second component to form a complex using the isopeptide bond.

8. A kit for self-assembling two molecules or components using an isopeptide bond, comprising one of the peptide linker 1 and the peptide linker 2 in the combination of peptide linkers according to claim 1, a nucleic acid molecule encoding the peptide linker 1 and the peptide linker 2 in the combination of peptide linkers, or a cell comprising a vector encoding the peptide linker 1 and the peptide linker 2 in the combination of peptide linkers.

9. A recombinant and synthetic peptide chain, comprising the peptide linker 1 and the peptide linker 2 in the combination of peptide linkers according to claim 2.

10. A nucleic acid molecule, comprising a nucleotide sequence encoding the peptide linker 1 and the peptide linker 2 in the combination of peptide linkers according to claim 2.

11. A vector, comprising the nucleic acid molecule according to claim 10.

12. A cell, comprising the vector according to claim 5.

13. A method for self-assembling two molecules or components using an isopeptide bond, comprising:

providing a first molecule or a first component comprising the peptide linker 1 in the combination of peptide linkers according to claim 2;

providing a second molecule or a second component comprising the peptide linker 2 in the combination of peptide linkers; and contacting the first molecule or the first component with the second molecule or the second component in a case of spontaneously forming an isopeptide bond between the peptide linker 1 and the peptide linker 2, such that the first molecule or the first component is self-assembled with the second molecule or the second component to form a complex using the isopeptide bond.

14. A kit for self-assembling two molecules or components using an isopeptide bond, comprising one of the peptide linker 1 and the peptide linker 2 in the combination of peptide linkers according to claim 2, a nucleic acid molecule encoding the peptide linker 1 and the peptide linker 2 in the combination of peptide linkers, or a cell comprising a vector encoding the peptide linker 1 and the peptide linker 2 in the combination of peptide linkers.

* * * * *